(12) United States Patent
Razansky et al.

(10) Patent No.: US 9,271,654 B2
(45) Date of Patent: Mar. 1, 2016

(54) THERMOACOUSTIC IMAGING WITH QUANTITATIVE EXTRACTION OF ABSORPTION MAP

(75) Inventors: Daniel Razansky, München (DE);
Vasilis Ntziachristos, München (DE);
Amir Rosenthal, Haifa (IL)

(73) Assignee: Helmholtz Zentrum Munchen Deutsches Forschungszentrum fur Gesundheit und Umwelt (GmbH), Neuherberg (DE)

( * ) Notice: Subject to any disclaimer, the term of this patent is extended or adjusted under 35 U.S.C. 154(b) by 614 days.

(21) Appl. No.: 13/381,207

(22) PCT Filed: Jun. 29, 2009

(86) PCT No.: PCT/EP2009/004687
§ 371 (c)(1),
(2), (4) Date: Jan. 27, 2012

(87) PCT Pub. No.: WO2011/000389
PCT Pub. Date: Jan. 6, 2011

(65) Prior Publication Data
US 2012/0123256 A1     May 17, 2012

(51) Int. Cl.
*A61B 5/00* (2006.01)
*G01N 21/17* (2006.01)

(52) U.S. Cl.
CPC ............ *A61B 5/0095* (2013.01); *A61B 5/0093* (2013.01); *G01N 21/1702* (2013.01); *A61B 5/0059* (2013.01); *G01N 21/17* (2013.01)

(58) Field of Classification Search
CPC ............................. A61B 5/0093; A61B 5/0095
See application file for complete search history.

(56) References Cited

U.S. PATENT DOCUMENTS

| | | | |
|---|---|---|---|
| 4,255,971 | A | 3/1981 | Rosencwaig |
| 4,343,993 | A | 8/1982 | Bining et al. |
| 4,385,634 | A | 5/1983 | Bowen |
| 4,646,756 | A | 3/1987 | Watmough et al. |

(Continued)

FOREIGN PATENT DOCUMENTS

| | | |
|---|---|---|
| EP | 0459392 | 12/1991 |
| EP | 133703 | 8/2003 |

(Continued)

OTHER PUBLICATIONS

Quantitative spatially resolved measurement of tissue chromophore concentrations using photoacoustic spectroscopy: application to the measurement of blood oxygenation and haemoglobin concentration, by Jan Laufer et al. pub. Phys. Med. Biol. 52 (2007) 141-168.*

(Continued)

*Primary Examiner* — Katherine Fernandez
*Assistant Examiner* — Michael Kellogg
(74) *Attorney, Agent, or Firm* — Stoel Rives LLP

(57) ABSTRACT

A method of thermoacoustic imaging of an object includes providing thermoacoustic signals representing a mechanical wave response to a delivery of electromagnetic energy into the imaged object, reconstructing an energy deposition image representing a local energy absorption within the object based on the thermoacoustic signals, and decomposing the energy deposition image into a quantitative absorption image representing a distribution of a local absorption coefficient in the object and at least one further image component.

22 Claims, 6 Drawing Sheets

(56) References Cited

U.S. PATENT DOCUMENTS

| | | |
|---|---|---|
| 4,770,183 A | 9/1988 | Groman et al. |
| 4,986,275 A | 1/1991 | Ishida et al. |
| 5,411,730 A | 5/1995 | Kirpotin et al. |
| 5,840,023 A | 11/1998 | Oraevsky et al. |
| 5,924,991 A | 7/1999 | Hossack et al. |
| 6,070,093 A | 5/2000 | Oosta et al. |
| 6,102,857 A | 8/2000 | Kruger |
| 6,173,604 B1 | 1/2001 | Xiang |
| 6,208,749 B1 | 3/2001 | Gutkowicz-Krusin et al. |
| 6,216,025 B1 | 4/2001 | Kruger |
| 6,263,221 B1 | 7/2001 | Chance et al. |
| 6,424,410 B1 | 7/2002 | Pelosi |
| 6,428,171 B1 | 8/2002 | Aoki et al. |
| 6,445,453 B1 | 9/2002 | Hill |
| 6,477,398 B1 | 11/2002 | Mills |
| 6,498,492 B1 | 12/2002 | Rezvani |
| 6,567,688 B1 | 5/2003 | Wang |
| 6,615,063 B1 | 9/2003 | Ntziachristos et al. |
| 6,641,798 B2 | 11/2003 | Achilefu et al. |
| 6,662,040 B1 | 12/2003 | Henrichs et al. |
| 6,700,459 B2 | 3/2004 | Raihn et al. |
| 6,760,609 B2 | 7/2004 | Jacques |
| 6,768,265 B1 | 7/2004 | Ives et al. |
| 7,005,653 B1 | 2/2006 | O'Connell et al. |
| 7,298,869 B1 | 11/2007 | Abernathy |
| 7,510,555 B2 | 3/2009 | Kanzius |
| 7,515,948 B1 | 4/2009 | Balberg et al. |
| 7,894,885 B2 | 2/2011 | Bartal et al. |
| 2002/0026106 A1 | 2/2002 | Khalil et al. |
| 2002/0048077 A1 | 4/2002 | Fukumoto |
| 2002/0073717 A1 | 6/2002 | Dean |
| 2002/0163735 A1 | 11/2002 | Detlef et al. |
| 2002/0193678 A1 | 12/2002 | Kruger |
| 2003/0023152 A1 | 1/2003 | Abbink et al. |
| 2003/0135110 A1 | 7/2003 | Leussier |
| 2004/0054268 A1 | 3/2004 | Esenaliev et al. |
| 2004/0059265 A1 | 3/2004 | Candy et al. |
| 2004/0067000 A1 | 4/2004 | Bates et al. |
| 2004/0127783 A1 | 7/2004 | Kruger |
| 2004/0176805 A1 | 9/2004 | Whelan |
| 2004/0181153 A1 | 9/2004 | Hall |
| 2004/0232321 A1 | 11/2004 | Miles et al. |
| 2004/0254457 A1 | 12/2004 | van der Weide |
| 2005/0150309 A1 | 7/2005 | Beard |
| 2005/0175540 A1 | 8/2005 | Oraevsky et al. |
| 2005/0234319 A1 | 10/2005 | Mandelis et al. |
| 2006/0064001 A1 | 3/2006 | Barbour |
| 2006/0084861 A1 | 4/2006 | Blank et al. |
| 2006/0184042 A1 | 8/2006 | Wang et al. |
| 2006/0256339 A1 | 11/2006 | Lowney et al. |
| 2006/0264717 A1 | 11/2006 | Pesach et al. |
| 2007/0015992 A1 | 1/2007 | Filkins et al. |
| 2007/0152144 A1 | 7/2007 | Quake |
| 2007/0197886 A1 | 8/2007 | Naganuma et al. |
| 2007/0238954 A1 | 10/2007 | White et al. |
| 2007/0238958 A1 | 10/2007 | Oraevsky et al. |
| 2007/0274580 A1 | 11/2007 | Ntziachristos et al. |
| 2008/0071172 A1 | 3/2008 | Bruck et al. |
| 2008/0118934 A1 | 5/2008 | Gerdes |
| 2008/0123083 A1 | 5/2008 | Wang et al. |
| 2008/0173093 A1 | 7/2008 | Wang et al. |
| 2008/0221647 A1 | 9/2008 | Chamberland et al. |
| 2008/0228073 A1 | 9/2008 | Silverman et al. |
| 2009/0024038 A1 | 1/2009 | Arnold |
| 2009/0038375 A1 | 2/2009 | Breuer et al. |
| 2009/0054763 A1 | 2/2009 | Wang et al. |
| 2009/0058746 A1 | 3/2009 | Delgado |
| 2009/0081122 A1 | 3/2009 | Rufenacht et al. |
| 2009/0192358 A1 | 7/2009 | Jaffer et al. |
| 2010/0022866 A1 | 1/2010 | Feke et al. |
| 2010/0078576 A1 | 4/2010 | Ntziachristos et al. |
| 2010/0249570 A1 | 9/2010 | Carson et al. |
| 2011/0001975 A1 | 1/2011 | Razansky et al. |
| 2011/0040176 A1 | 2/2011 | Razansky et al. |
| 2011/0201914 A1 | 8/2011 | Wang et al. |
| 2011/0208057 A1 | 8/2011 | Oikawa |
| 2011/0231160 A1 | 9/2011 | Suzki |
| 2011/0282192 A1 | 11/2011 | Axelrod et al. |
| 2011/0301453 A1 | 12/2011 | Ntziachristos et al. |
| 2011/0306865 A1 | 12/2011 | Thornton et al. |
| 2012/0029829 A1 | 2/2012 | Li et al. |
| 2012/0150012 A1 | 6/2012 | Fujimoto et al. |
| 2013/0041267 A1 | 2/2013 | Ntziachristos et al. |
| 2013/0312526 A1 | 11/2013 | Oishi |
| 2014/0114187 A1 | 4/2014 | Rozental et al. |
| 2014/0198606 A1 | 7/2014 | Morscher et al. |
| 2014/0336505 A1 | 11/2014 | Ripoll Lorenzo et al. |
| 2014/0363066 A1 | 12/2014 | Ntziachristos et al. |

FOREIGN PATENT DOCUMENTS

| | | |
|---|---|---|
| EP | 1561424 | 8/2005 |
| EP | 2695893 | 8/2012 |
| JP | 09219563 | 8/1997 |
| JP | 2004351023 | 12/2004 |
| JP | 2007/307007 | 11/2007 |
| JP | 2010125260 | 6/2010 |
| JP | 2012170762 | 9/2012 |
| WO | WO2004/068405 | 8/2004 |
| WO | WO2006/061829 | 6/2006 |
| WO | WO2006/063246 | 6/2006 |
| WO | WO2007/084771 | 7/2007 |
| WO | WO2007/100937 | 9/2007 |
| WO | WO2007/111669 | 10/2007 |
| WO | WO2008/018082 | 2/2008 |
| WO | WO2008/101019 | 8/2008 |
| WO | 2009/055095 A1 | 4/2009 |
| WO | 2010/009747 A1 | 1/2010 |
| WO | WO2011/000389 | 1/2011 |
| WO | WO2011/072198 | 6/2011 |
| WO | WO2011/137385 | 11/2011 |
| WO | WO2012/108170 | 8/2012 |
| WO | WO2012/108172 | 8/2012 |
| WO | WO2012/137855 | 10/2012 |
| WO | WO2012/150721 | 11/2012 |
| WO | WO2013/167147 | 11/2013 |
| WO | WO2013/185784 | 12/2013 |
| WO | WO2014/066150 | 5/2014 |

OTHER PUBLICATIONS

Digital Image Processing: PIKS Scientific Inside by William K. Pratt, pub. Wiley-Interscience; 4 edition (Feb. 9, 2007); ISBN: 0471767778; Chapter 4.*

Sugiyama et al., 'Character Pattern Recognition Utilizing Independent Component', Proceedings of the 44th Conference of the Institute of Systems, Control and Information Engineers (ISCIE), p. 457-458, English abstract, 2000.

Taruttis et al., 'Motion Clustering for Deblurring Multispectral Optoaxoustic Tomography Images of the Mouse Heart', Journal of Biopmedical Optics, vol. 17, No. 1, pp. 16009-1 to 16009-4, Jan. 2012.

Taruttis et al., 'Imaging the Small Animal Cardiovascular System in Real-Time with Multispectral Optoacoustic Tomography', Proc of SPIE, vol. 7899, pp. 789913-1 to 789913-8, 2011.

Buehler et al., 'Video Rate Optoacoustic Tomography of Mouse Kidney Perfusion', Optics Letters, vol. 35, No. 14, pp. 2475-2477, Jul. 15, 2010.

Glatz et al., 'Blind Source Unmixing in Multi-Spectral Optoacoustic Tomography', Optics Express, vol. 19, No. 4, pp. 3175-3184, Feb. 14, 2011.

Morscher et al., 'Spectral Unmixing Using Component Analysis in Multispectral Optoacoustic Tomography', Proc SPIE, vol. 8089, 2011.

Morscher et al., 'Blind Spectral Unmixing to Identify Molecular Signatures of Absorbers in Multispectral Optoacoustic Tomography', Proc SPIE, Photons Plus Ultrasound: Imaging and Sensing, vol. 7899, 2011.

Office Action dated Jul. 31, 2014 for U.S. Appl. No. 13/386,491.

Ku et al., 'Thermoacoustic and Photoacoustic Tomography of Thick Biologial Tissues Toward Breast Imaging', Technogy in Cancer Research & Treatment, ISSN 1533-0346, vol. 4, No. 5, dated Oct. 2005.

(56) References Cited

OTHER PUBLICATIONS

Office Action dated Aug. 2, 2013 for U.S. Appl. No. 13/386,491.
Yuan et al., 'Quantitative Photoacoustic Tomography: Recovery of Optical Absorption coefficient Maps of Haterogeneous Media', Applied Physics Letters 88:231101, 2006.
Razansky et al., 'Multispectral Photoacoustic Imaging of Fluorochromes in Small Animals', Optics Letters, vol. 23, No. 19, pp. 2891-2893, Oct. 1, 2007.
Rosenthal et al., 'Quantitative Optoacoustic Signal Extraction Using Sparse Signal Repesentation', IEEE Transactions on Medical Imaging, vol. 28, No. 12, pp. 1997-2006, 2009.
Xu et al., 'Exact Frequency-Domain Reconstruction for Thermoacoustic Tomography—I: Planar Geometry', IEEE Transactions on Medical Imaging, vol. 21, No. 7, pp. 823-828, 2002.
Oraevsky et al., 'Direct Measurement of Laser Fluence Distribution and Optoacoustic Imaging in Heterogeneous Tissues', Proc SPIE 2323, Laser Interactions with Hard and Soft Tissue 11, 37, 1995.
Karabutov et al., 'Optoacoustic Measurement of Optical Properties of Turbid Media', Proc. SPIE vol. 4749, pp. 288-298, 2002.
Razansky et al., 'Multispectral Opto-Acoustic Tomography of Deep-Seated Fluorescent Proteins in Vivo', Nature Photonics, 3, 412-417, 2009.
Schulz et al., 'Experimental Fluorescence Tomography of Tissues with Noncontact Measurements', IEEE Transactions on Medical Imaging, Vo. 23, No. 4, oo 492-500, 2004.
Ripoll et al., 'Free-Space Propagation of Diffuse Light: Theory and Experiments', Phys. Rev, Lett., vol. 91, No. 10, pp. 103901-1-103901-6, 2003.
Zibulevsky et al., 'Blind Source Separation by Sparse Decomposition', ICA, Principle and Practice, Chapter 7, Cambridge, 2001.
Capps, "Near Field or Far Field?", EDN Network, www.ednmag.con Aug. 16, 2001, p. 95-102.
Office Action dated Jun. 3, 2013 for U.S. Appl. No. 12/867,265.
Office Action dated Jun. 18, 2013 for U.S. Appl. No. 13/055,552.
U.S. Appl. No. 12/867,265, filed Sep. 20, 2010, Razansky et al.
U.S. Appl. No. 13/386,491, filed Apr. 5, 2012, Razansky et al.
U.S. Appl. No. 13/055,552, filed Feb. 23, 2011, Razansky et al.
Ash et al., 'Super-Resolution Aperture Scanning Microscope', Nature, vol. 237, Jun. 30, 1972, pp. 510-512.
Larin et al., 'Monitoring of Tissue Coagulation During Thermotherapy Esing Optoacoustic Technique', Journal of Physics D: Applied Physics, 2005, vol. 38, pp. 2645-2653.
'American National Standard for Safe Use of Lasers', Laser Institute of America, ANS1Z136.1, 2007 (revision of ANS1Z136.1 2000).
Intes et al. 'Projection Access Order in Algebraic Reconstruction Technique for Diffuse Optical Tomography', Phys Med Biol, 2002, vol. 47, pp. N1-N10.
Office Action dated Dec. 7, 2012 for U.S. Appl. No. 13/055,552.
Vinegoni et al., 'In vivo Imaging of *Drosophila metanogaster* Pupae with Mesoscopic Fluorescence Tomography', Nature Methods, Jan. 2008, vol. 5 No. 1, pp. 45-47 and Supplementary Notes.
Zacharakis et al., 'volumetric Tomography of Fluorescent Proteins Through Small Animals in Vivo', PNAS, Dec. 20, 2005, vol. 102 No. 51, pp. 18252-18257.
U.S. Appl. No. 14/102,328, filed Dec. 10, 2013, Kacprowicz.
U.S. Appl. No. 14/102,250, filed Dec. 10, 2013, Razansky et al.
Office Action dated Jan. 14, 2014 for U.S. Appl. No. 13/055,552.
Office Action dated Jan. 29, 2014 for U.S. Appl. No. 12/867,265.
Laufer, J. et al., "Quantiative Spatially Resolved Measurement of Tissue Chromophore Concentrations Using Photoacoustic Spectroscopy: Application to the Measurement of Blood Oxygenation and Haemoglobin Concentration," *Phys. Med. Biol.*, 2007, vol. 52, pp. 141-168
Chen, S.S. et al., "Atomic Decomposition by Basis Pursuit," *SIAM Review*, vol. 43, No. 1, pp. 129-159.
Razansky, D. et al., Hybrid Photoacoustic Fluorescence Molecular Tomography Using Finite-Element-Based Inversion, *Med. Phys.*, Nov. 2007, vol. 34, No. 11, pp. 4293-4301.
Jetzfellner, T. et al., "Performance of Iterative Optoacoustic Tomography with Experimental Data," *Applied Physics Letters*, 2009, vol. 95, pp. 013703-1 to 013703-3.
Cox, B.T. et al., Gradient-Based Quantiative Photoacoustic Image Reconstruction for Molecular Imaging, *Proc. of SPIE*, 2007, vol. 6437, pp. 6431T-1 to 6431T-10.
Cox, B.T. et al., "Two-Dimensional Quantitative Photoacoustic Image Reconstruction of Absorption Distributions in Scattering Media by Use of a Simple Iterative Method," *Applied Optics*, Mar. 10, 2006, vol. 45, No. 8 pp. 1866-1873.
Paltauf, G. et al., "Iterative Reconstruction Algorithm for Optoacoustic Imaging," *J. Acoust. Soc. Am.*, Oct. 2002, vol. 112, No. 4, pp. 1536-1544.
Jiang, H. et al., "Spatially Varying Optical and Acoustic Property Reconstruction Using Finite-Element-Based Photoacoustic Tomography," *J. Opt. Soc. Am.*, Apr. 2006, vol. 23, No. 4, pp. 878-888.
U.S. Appl. No. 13/399,272, filed Nov. 6, 2014, Kellnberger et al.
Office Action dated Nov. 26, 2014 for U.S. Appl. No. 13/386,491.
Office Action dated Dec. 26, 2014 for U.S. Appl. No. 12/867,265.
Xu et al., 'Universal Back-Projection Algorithm for Photoacoustic Computed Tomography', The American Physical Society,Physical Review, vol. E71, No. 1, pp. 016706, 2005.
Skolnik, Radar Handbook, McGraw Hill, Chapter 8, 2008.
Ye, 'PSTD Method of Thermoacoustic Tomography (TAT) and Related Experimental Investigation', Dissertation, 2009.
Telenkov et al., 'Frequency-Domain Photothermoacoustics: Alternative Imaging Modality of Biological Tissues', Journal of Applied Physics, vol. 105, p. 102029, 2009.
Fan et al., 'Development of a Laser Photothermoacoustic Frequency-Swept System for Subsurface Imaging: Theory and Experiment', J. Acoust. Soc. Am., 116(6), 2004.
Skolnik, Introduction to Radar Systems, Chapter 6.5, McGraw Hill, 2001.
Skolnik, Introduction to Radar Systems, Chapter 11.5, McGraw Hill, 1981.
Rosenthal et al., 'Fast Semi-Analytical Model-Based Acoustic Inversion for Quantitative Optoacoustic Tomography', IEEE Transactions on Medical Imaging, vol. 29, No. 6, Jun. 2010.
Baddour, 'Theory and Analysis of Frequency-Domain Photoacoustic Tomography', J. Acoust. Soc. Am., 123(5), pp. 2577-2590, 2008.
Paltauf et al., 'Three-Dimensional Photoacoustic Tomography Using Acoustic Line Detectors', Soc. Opt. Eng., vol. 6437,pp. 1-10, 2007.
Maslov et al., 'Photoacoustic Imaging of Biological Tissue with Intensity-Modulated Continuous-Wave Laser', Journal of Biomedical Optics, vol. 13, No. 2, pp. 024006, 2008.
Kak et al., 'Principles of Computerized Tomographic Imaging', IEEE Press, Chapters 3 and 6, 1988.
International Preliminary Report dated Dec. 24, 2014 for PCT/EP2012/002466.
Wang, 'Multiscale Photoacoustic Microscopy and Computed Tomography', Nature Photonics, Review Article, 2009.
Zhang et al., 'Collecting Back-Reflected Photons in Photoacoustic Microscopy', Optics Express, vol. 18, No. 2, Jan. 18, 2010.
Wang et al., 'Photoacoustic Tomography: In Vivo Imaging from Organelles to Organs', Science, 335(6075), Mar. 23, 2012.
Yao et al.; 'Photoacoustic Tomography: Fundamentals, Advances and Prospects', contrast Media Mol Imaging 6(5), 2011.
Li et al., 'Fast-Scanning Reflection-Mode Integrated Photoacoustic and Optical-coherence Microscopy', Proc. of SPIE, vol. 7564, 2010.
Ntziachristos, 'Going Deeper than Microscopy: The Optical Imaging Frontier in Biology', Nature Methods, vol. 7, No. 8, 2010.
Office Action dated Oct. 29, 2014 for U.S. Appl. No. 13/055,552.
Aguirre et al., 'A curved Array Photoacoustic Tomography System for Small Animal Imaging', Proc, SPIE 6437:OV1-OV10, 2007.
Allen et al., 'Dual Wavelength Laser Diode Excitation Source for 2D Photoacoustic Imaging', Proc. SPIE 6437: U1-U9, 2007.
Erpelding et al., 'Three-Dimensional Photoacoustic Imaging with a Clinical Two-Dimensional Matrix Ultrasound Transducer', Photons Plus Ultrasound: Imaging and Sensing, Proc of SPIE, vol. 7899, 2011.

(56) References Cited

OTHER PUBLICATIONS

Office Action dated Jan. 28, 2014 for U.S. Appl. No. 13/386,491.
Office Action dated Jul. 7, 2015 for U.S. Appl. No. 13/386,491.
Office Action dated Jul. 14, 2015 for U.S. Appl. No. 14/102,250.
Office Action dated Jul. 14, 2015 for U.S. Appl. No. 14/102,328.
Office Action dated Jul. 30, 2015 for U.S. Appl. No. 13/055,552.
Office Action dated Aug. 30, 2012 for U.S. Appl. No. 12/684,816.
Office Action dated Oct. 2, 2015 for U.S. Appl. No. 12/867,265.
Philips. White Pate for iU22 with X7-2 Probe, 2010, 1 pg, internet. https://web.archive.org/web/20100908015304/http://healthcare.philips.com/main/products/ultrasound/transducers/7x_2.wpd.
Song, 'High-Speed Photoacoustic Microscopy in Vivo', Ph.D. Thesis, School of Eng. & Appl. Sci., Washington University, Saint Louis, 133 pgs, 2010.
Viator et al., 'Clinical Testing of a Photoacoustic Probe for Port-Wine Stain Depth Determination', Lasers Surg. Med. 30:141-148, 2002.
Yin et al., 'Tomographic Imaging of Absolute Optical Absorption Coefficient in Turbid Media Using combined Photoacoustic and Diffusing Light Measurements', Optics Letters, vol. 32 No. 17, pp. 2556-2558, 2007.
Office Action dated Dec. 3, 2015 for U.S. Appl. No. 14/141,773.
Xu, Minghua et al., "Time-Domain Reconstruction for Thermoacoustic Tomography in a Spherical Geometry", IEEE Transactions on Medical Imaging vol. 21, No. 7, Jul. 2002, pp. 814-822.

\* cited by examiner

THERMOACOUSTIC IMAGING WITH QUANTITATIVE EXTRACTION OF ABSORPTION MAP

RELATED APPLICATIONS

This is a §371 of International Application No. PCT/EP2009/004687, with an international filing date of Jun. 29, 2009 (WO 2011/000389 A1, published Jan. 6, 2011), the subject matter of which is incorporated by reference.

TECHNICAL FIELD

This disclosure relates to methods of creating thermoacoustic images of an object, wherein a quantitative image representing a local map of absorption within the object is reconstructed based on thermoacoustic signals obtained from a mechanical wave response to a delivery of electromagnetic energy into the imaged object. Furthermore, the disclosure relates to thermoacoustic imaging devices configured for conducting the above methods. Applications are available, e.g., in medical imaging or material investigations. In particular, the methods can be used for accurate extraction of biomarker concentration in noninvasive small animal and clinical imaging, e.g., for characterization of vascular trees, tumor angiogenesis, blood oxygenation or in molecular imaging studies with various targeted contrast agents, including dyes, light-absorbing nano-particles and fluorochromes.

BACKGROUND

Thermoacoustic imaging is a fast evolving non-invasive modality for high-resolution mapping of local energy deposition in tissue. In particular, optoacoustic (or photoacoustic) tomography aims at reconstructing maps of local optical absorption coefficient of tissue, which can subsequently be related to the concentration of certain intrinsic and exogenously-administered biomarkers and probes. The imaging is performed by illuminating the object or region of interest with short high-power electromagnetic pulses, in particular laser pulses, thus creating an instantaneous temperature elevation and thermal expansion within it. As a result, high-frequency acoustic fields are formed that propagate towards the object's boundary where they can be subsequently recorded. In this way, an image representing local energy deposition within the object can be reconstructed by collecting tomographic information around the object and using optoacoustic inversion algorithms.

While image formation in optoacoustics can be performed in several ways, they require some mathematical inversion for image formation from raw measurements of the optoacoustic response. Ideally, the reconstructed image should represent a quantitative map of the underlying absorption properties of the imaged tissue, which can be subsequently related to distribution of various tissue chromophores and biomarkers. However, in most cases, the detected acoustic signals represent the overall local energy deposition in the imaged object. Thus, the initial optoacoustic image requires further analysis to extract the relevant information. One apparent difficulty is the highly heterogeneous nature of common biological tissues in the visible and near-infrared spectra. This in turn causes highly non-uniform distribution of excitation light within the imaged object owing to scattering and attenuation. In addition, inaccuracies in the currently used optoacoustic inversion models further hinder image quantification.

With further detail, current optoacoustic inversion techniques, which produce the deposited energy image from the acoustic fields, suffer from quantification inaccuracy, low spatial resolution, or inflexibility owing to the absence of appropriate methods to accurately account for experimental and physical propagation factors. Algorithms that currently exist for inversion and image formation can be divided into two groups: those based on a closed form analytical solution of the optoacoustic wave equation and those based on numerical calculations.

The first kind of algorithms refers to back-projection algorithms in which the reconstruction of the optoacoustic image is given as an integral over the measured signals similar to linear Radon-based transformations. These reconstruction methods are usually based on several approximations to the exact optoacoustic equation, thus creating substantial artifacts in the reconstruction. Moreover, the back-projections algorithms are incapable of incorporating multiple instrumentation-based factors into the inversion. For example, it may not be possible to directly take into account the frequency response of the ultrasonic detector or its finite size in the back-projection algorithms.

The second kind of algorithms is model-based inversion in which the acoustic propagation problem is solved numerically and iteratively in either the frequency or time domains by using, e.g., finite-elements method. Model-based thermoacoustic inversion schemes were previously attempted by H. Jiang et al. ("J. Opt. Soc. Am.," vol. A 23, 2006, p. 878-888) and by G. Paltauf et al. ("The Journal of the Acoustical Society of America," vol. 112(4), 2002, p. 1536-44). However, the computational complexity involved with these particular methods has limited their achievable resolution and hindered practical implementations.

Since in most realistic imaging scenarios it is practically impossible to uniformly illuminate the entire region of interest, the initially formed image will represent a coupled map of energy deposition in tissue and absorption, rather than the required quantified absorption coefficient values. In other words, the thermoacoustic image will comprise a product between the optical absorption and the light fluence within the object. Thus, targets deep in the object may appear weaker than targets having similar optical absorption but located close to the illuminated surface. Quantitative reconstructions, especially of volumetric phenomena, were not previously possible owing to limitations in both optoacoustic inversion algorithms, image normalization methods and corresponding system implementations. These inaccuracies limit applicable areas of conventional (qualitative) optoacoustic imaging. Consequently, systems reported so far for opto-acoustic imaging compromise the image quality and quantification, a performance that worsens with depth or volumetric imaging.

Moreover, when analyzing multi-spectral optoacoustic images, i.e., images obtained for several excitation wavelengths, spectral changes in the light fluence may dominate the optoacoustic images and obfuscate the absorption spectrum of targets of interests. This limits the use of Multi-Spectral Optoacoustic Tomography (MSOT), which is described, e.g., in PCT/EP2008/006142 (unpublished on the priority date of the present specification), for mapping the concentration of various targets with spectrally dependant absorptions.

Methods have been proposed for the extraction of the absorption coefficient and quantification improvement. Some approaches are based on solving the diffusion equation that governs light propagation to find and correct for light distribution within the object (B. T. Cox et al. in "Applied Optics," vol. 45, p. 1866-1875, 2006; B. T. Cox B T et al in "Proc SPIE," 6437, 64371T-1-10, 2007). Once a hypothesized light distribution solution is found, it is used to normalize the optoacoustic image and to extract the absorption coefficient. As a further step, the extracted absorption can be used to recalculate the light distribution within the object, which in turn is used to re-normalize the optoacoustic image. This process can be repeated in an iterative manner until convergence is achieved.

However, the above methods rely on empirical assumptions regarding optical properties of the tissue and other experimental parameters. Therefore they suffer from convergence instability that limits the ability for robust quantification accuracy (Jetzfellner et al. in "Appl. Phys. Lett.," 95(1), 2009).

The main deficiency of optoacoustic image normalization methods is that they rely on a light fluence distribution that is modeled based on hypothesized light propagation equations, such as the light diffusion equation. However, these equations require accurate prior knowledge of the optical properties of the medium, which are usually largely unknown, in particular scattering but also absorption. In most cases, an estimated value or structure is prescribed to the optical parameters of the medium. In practice, it has been found however that even small errors in the assigned optical properties can lead to large errors in the reconstruction. Moreover, if an iterative self-correcting approach is applied, convergence to accurate values is rarely possible owing to modeling inaccuracies. Thus, as to date, reliable performance has not yet been demonstrated using these techniques for in-vivo data, i.e., for media where light distribution is spatially heterogeneous.

The above limitations are not restricted to optoacoustics. The corresponding disadvantages generally occur in other thermoacoustic imaging methods wherein, e.g., radiofrequency pulses are used for delivering energy to the object instead of the object illumination with laser pulses.

It could therefore be helpful to provide improved methods and preferred geometry for thermoacoustic imaging capable of avoiding disadvantages and restrictions of conventional qualitative reconstruction techniques. In particular, it could be helpful to provide accurate thermoacoustic imaging methods capable of quantitative imaging with increased precision and reproducibility, not only in surface and subsurface regions, but also volumetrically in entire objects. Furthermore, it could be helpful to provide thermoacoustic imaging device implementations capable of avoiding disadvantages and restrictions of conventional techniques.

SUMMARY

We provide a method of thermoacoustic imaging of an object including providing thermoacoustic signals representing a mechanical wave response to a delivery of electromagnetic energy into the imaged object, reconstructing an energy deposition image representing a local energy absorption within the object based on the thermoacoustic signals, and decomposing the energy deposition image into a quantitative absorption image representing a distribution of a local absorption coefficient in the object and at least one further image component.

We also provide a method of thermoacoustic imaging including providing thermoacoustic signals representing a mechanical wave response to a delivery of electromagnetic energy to an imaged object, and reconstructing an energy deposition image representing a local energy deposition within the object based on the thermoacoustic signals, the reconstructing step including a matrix-based acoustic inversion of the thermoacoustic signals utilizing an inverted model matrix.

We further provide an imaging device for thermoacoustic imaging of an object including a signal collecting device that collects thermoacoustic signals representing a mechanical wave response to a delivery of electromagnetic energy into the imaged object, an energy deposition image reconstruction device that reconstructs an energy deposition image representing a local energy deposition within the object based on collected thermoacoustic signals, and an absorption image decomposition device that decomposes the energy deposition image into a quantitative absorption image representing a distribution of a local absorption coefficient in the object and at least one further image component.

We still further provide an imaging device for optoacoustic imaging of an object including an energy-deposition image reconstruction device that reconstructs an energy deposition image representing a local energy deposition within the object based on the thermoacoustic signals, wherein the energy deposition image reconstruction device comprises an inversion circuit that subjects the thermoacoustic signals to a matrix-based acoustic inversion utilizing an inverted model matrix.

We further yet provide a computer program on a computer-readable medium, with a program code that carries out the method.

We also further provide an apparatus including a computer-readable storage medium containing program instructions that carries out the method.

DETAILED DESCRIPTION

Figure 1:
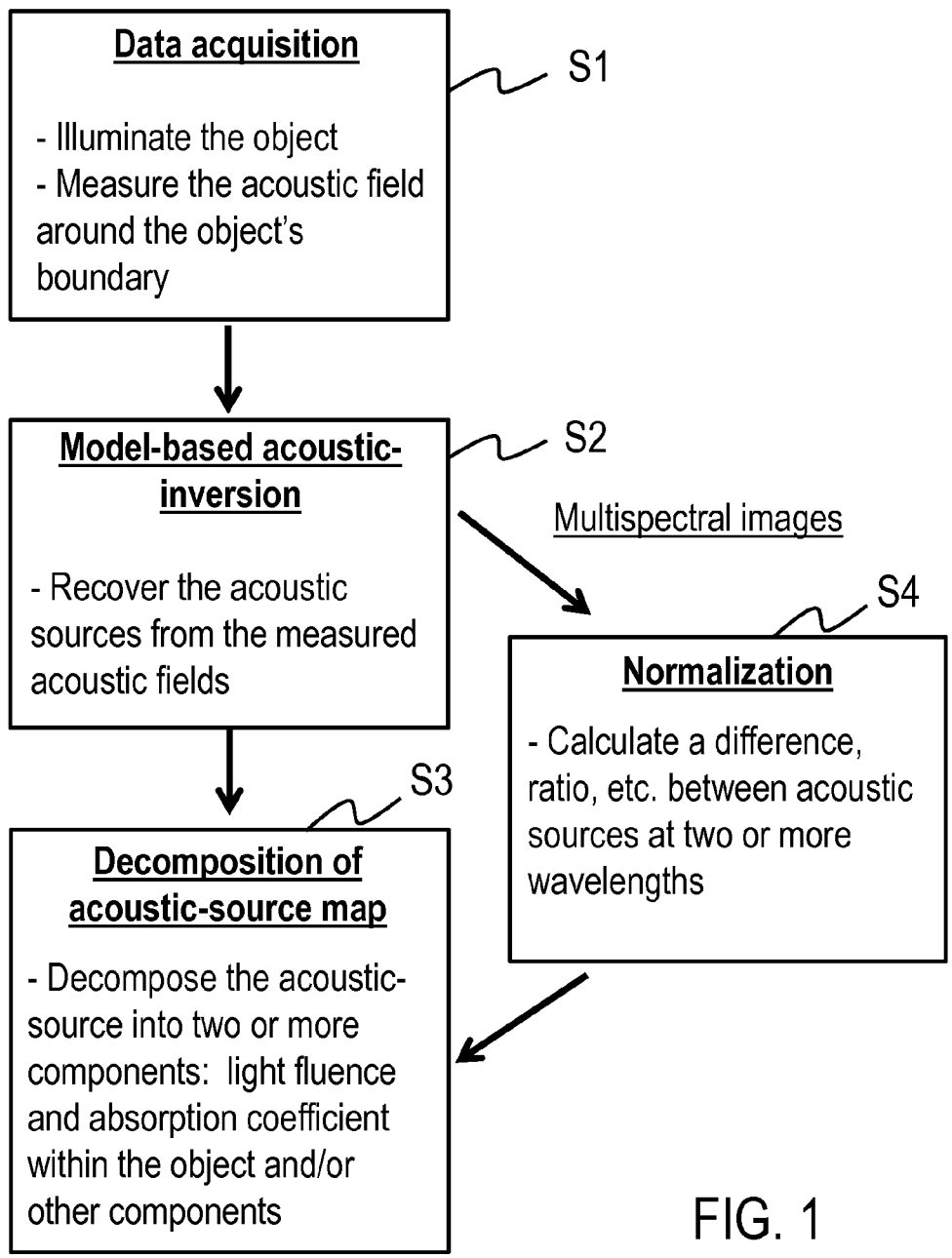
FIG. 1 shows an overview of main steps of our imaging methods.

We provide a method of thermoacoustic imaging, wherein an energy deposition image may be subjected to a decomposition into a quantitative absorption image representing a geometric distribution of a local absorption coefficient in the object and at least one further image component. First, thermoacoustic signals are provided representing a mechanical wave response to a delivery of electromagnetic energy (excitation energy) into the imaged object. Provision of the thermoacoustic signals comprises, e.g., collecting or recording the signals with an imaging device or delivering the signals from a data source. Subsequently, based on the thermoacoustic signals at least one energy deposition image representing a local energy absorption within the object is reconstructed. The reconstruction may comprise a conventional analytical or numerical method, e.g., an iterative propagation model-based simulation, or preferably a matrix-based optoacoustic inversion outlined below. Finally, the energy deposition image is subjected to the decomposition into the quantitative absorption image and the at least one further image component.

Depending on the wavelength of the excitation energy used, the local absorption coefficient distribution (absorption image) comprises, e.g., an optical absorption distribution or an electric conductivity distribution. The at least one further image component typically comprises a distribution of the excitation energy in the object. Alternatively or additionally, the at least one further image component comprises an image of one or more from the following: a distribution of the optical scattering coefficient, a distribution of speed of sound, an image representing local polarization state, an electric or magnetic field distribution, a dielectric constant distribution, a thermoelastic expansion coefficient distribution, a heat capacity distribution, and a distribution of a certain biomarker.

The image decomposition representing the essential part of the method above provides a new quantification methodology of thermoacoustic tomographic reconstructions under highly heterogeneous illumination conditions, as occurring, e.g., with realistic wholebody imaging scenarios. Advantageously, the image decomposition method does not depend on selecting an accurate photon-propagation model to account for the fluence non-uniformities within the medium. Instead, it decomposes the image to its principal components by using techniques from the field of sparse representation. The decomposition method relies on different spatial characteristics of the absorption coefficient and the energy density (fluence), in particular optical energy or photon density, within the medium. We found that the fluence is smooth and global, while the absorption coefficient has more localized and often sharp spatial transients in most imaging applications like medical imaging or imaging in material sciences. By using the sparse-representation based decomposition, these different characteristics are exploited to extract both the absorption coefficient and the energy deposition density within the imaged object from the thermoacoustic image. In contrast to previous methods, this image normalization method is not based on the solution of theoretical light transport equations and offers robust performance, as it does not require explicit knowledge of the illumination geometry, optical properties of the object and other unknown or loosely defined experimental parameters. The method is therefore ideally suited for practical implementations in varying complexity tomographic schemes including multi-projection illumination systems and multi-spectral optoacoustic tomography studies of tissue biomarkers.

We also provide a method of thermoacoustic imaging of an object, wherein thermoacoustic signals representing a mechanical wave response to a delivery of electromagnetic energy to the object may be used for reconstructing an energy deposition image representing a local energy deposition within the object and wherein the reconstructing step includes a matrix-based optoacoustic inversion of the thermoacoustic signals utilizing a forward model matrix.

The matrix-based optoacoustic inversion representing the essential part of this method provides a novel semi-analytical model-based inversion method for quantitative thermoacoustic image reconstruction. In contrast to back projection-like algorithms, the method is not based on an analytical solution to the inverse problem. Instead, the forward problem is reformulated in matrix relation, which is subsequently inverted. Advantageously, thermoacoustic signal generation and propagation presents a linear forward problem, therefore this type of optimization problem has only one single minimum. In addition, the model matrix is sparse, thus enabling efficient inversion algorithms to be used. Ideally, the inversion can yield artifact-free quantified thermoacoustic image reconstructions. As a further advantage, many additional linear effects can be added to the model matrix, while using the same matrix-inversion algorithm. Thus, the forward model is highly flexible and can be used to model a variety of linear attenuation and dispersion effects, for example, by taking the frequency response and spatial response of the detector into account as well as acoustic coupling, dispersion and other propagation aspects.

The semi-analytical solution is exact for piecewise planar acoustic-source functions. Thus, the solution is exact for a planar interpolation of the acoustic-source functions. This significantly improves the accuracy and computational speed associated with the forward model. Using this solution, the model matrix can be constructed, connecting the measured acoustic signals with the thermoacoustic image. By inverting the matrix relation, the thermoacoustic image is recovered. The matrix elements depend only on the setup geometry, and thus can be calculated before the experiment is performed. The inversion of the matrix relation can also be preformed beforehand by calculating the pseudo-inverse of the matrix. Once the experiment is performed, the inversion amounts to multiplying the pre-calculated pseudo-inverse with a vector containing the measured data—a computation that can in principle be performed in real time. Numerical and experimental tests have shown that the reconstruction algorithm does not suffer from back projection-related reconstruction artifacts and renders an accurate high-resolution map of laser energy deposition in the imaged object.

Apparently, the matrix model-based approach has several advantages over back-projection algorithms. First, it eliminates image artifacts associated with the approximated back-projection formulations, i.e., no negative absorption values are produced and the reconstructed image corresponds to the true light attenuation and energy deposition within the object. Clearly, since back-projection falsely emphasizes edges and fast image variations by producing large negative overshoots, it is capable of producing 'good looking' high-contrast images. However, due to its approximate formulation, it fails to reproduce the correct and quantitative image of the actual laser energy deposition in tissue and the underlining optical absorption values. This property is especially important for quantitative imaging applications, i.e., molecular imaging studies, in which obtaining the correct absorption maps is of high importance. Second, the method admits generalization of the forward solution to a more comprehensive acoustic propagation models without changing the inversion procedure. Finally and importantly, the model-based inversion can be seamlessly adapted to any detection geometry. Unlike in the conventional analytical inversion formulation, the position of the detectors is not restricted to specific geometries.

We provide an imaging device for thermoacoustic imaging of an object comprising a signal collecting device, a reconstruction device, and a decomposition device. The imaging device in particular is configured for implementing one of the methods of the above first and seconds aspects. The signal collecting device is an apparatus which is configured for collecting thermoacoustic signals in response to a delivery of electromagnetic energy into the imaged object. The signal collecting device is connected with the reconstruction device, which is arranged for processing the thermoacoustic signals. The reconstruction device is adapted for reconstructing an energy deposition image representing a local energy deposition within the object based on collected thermoacoustic signals. For implementing the above second method described above, the reconstruction device preferably comprises an inversion circuit being adapted for subjecting the thermoacoustic signals to a matrix-based optoacoustic inversion utilizing an inverted model matrix. Furthermore, the reconstruction device is connected with the decomposition device, which is adapted for decomposing the energy deposition image into a quantitative absorption image representing a distribution of a local absorption coefficient in the object and at least one further image component.

We further provide an imaging device for thermoacoustic imaging of an object comprising a reconstruction device being adapted for reconstructing the energy deposition image representing a local energy deposition within the object based on thermoacoustic signals, wherein the reconstruction device comprises an inversion circuit being adapted for subjecting the thermoacoustic signals to a matrix-based optoacoustic inversion utilizing an inverted model matrix.

We can thus identify systems and methods that achieve mapping of the absorbed energy deposition within the object from the measured acoustic signals and extract the absorption coefficient from this mapping by sparsely representing the mapping in a function library (function basis). Each aspect represents an independent subject. However, their combination is preferably implemented for achieving maximum imaging performance.

Preferably, the delivered electromagnetic energy comprises photon energy in the optical spectrum, i.e., the object is illuminated with light. The illumination light comprises at least one characteristic wavelength of at least 1 nm, preferably at least 400 nm, particularly preferred at least 650 nm, and below 5000 nm, preferably below 1200 nm, particularly preferred below 850 nm. In this instance, the signal collecting device includes a laser source device being adapted for emitting light pulses, preferably in the visible or near-infrared spectra. The light pulses preferably have a duration below 1 µs, particularly preferred below 50 ns.

Typically, the illumination light comprises one single illumination wavelength and/or one single light polarization. Accordingly, the energy deposition image can be reconstructed based on the thermoacoustic signals acquired at the single illumination wavelength and/or the single light polarization.

Alternatively, the information content of the quantitative imaging advantageously can be increased if the illumination light comprises multiple different excitation wavelengths and/or multiple different light polarizations. In this instance, multiple energy deposition images can be separately reconstructed based on the thermoacoustic signals separately acquired at the different illumination wavelengths and/or the different light/field polarizations. As a further option, the energy deposition image can be reconstructed based on a combination of the thermoacoustic signals acquired at the different illumination wavelengths and/or the different light/field polarizations. The combination of the thermoacoustic signals comprises linear or nonlinear signal superpositions, e.g., subtractions, summations, products, ratios or the like.

Alternatively, the delivered electromagnetic energy may comprise pulses in the radiofrequency or microwave spectral regions, preferably with pulse durations below 1 µs, most preferably with pulse durations below 50 ns. Accordingly, the signal collecting device may include radiation source being adapted for irradiating the imaged object with the radiofrequency pulses.

The thermoacoustic signals can be subjected to a pre-processing before the image reconstruction. Advantageously, pre-processing by an analog or digital signal processing operation, e.g., filtering, integration, differentiation, may improve the result of the image reconstruction.

With the image reconstructing step using the matrix-based optoacoustic inversion of the thermoacoustic signals, the elements of the model matrix can be chosen in dependency on linear effects influencing the thermoacoustic signal generation and propagation. Preferably, the model matrix is constructed in dependency on the geometry of a mechanical wave detector device collecting the thermoacoustic signals. Alternatively or additionally, the model matrix is constructed in dependency on at least one of an acoustic heterogeneity of the object, a geometric profile of the delivered electromagnetic energy in the imaged object, a frequency response of an acoustic-signal recording device utilized for collecting the thermoacoustic signals and a result of the decomposing step. Advantageously, the model matrix elements are mostly independent of the absorption properties of the object.

Particularly preferably, a logarithmic representation of the reconstructed energy deposition image is provided for the image decomposing step. Thus, the contributions of the absorption image and the at least one further image component are obtained as separate summands. Subsequently, the energy deposition image decomposing step comprises a calculation of the quantitative absorption image and the at least one further image component as summands of the logarithmic representation of the energy deposition image. To conduct these steps, the imaging device includes the decomposition device including a logarithm circuit and a processor calculating the quantitative absorption image and the at least one further image component.

Each of the summands preferably is provided as expansions in complementary libraries. The quantitative absorption image is represented as an expansion in a first library (a collection of functions, e.g., a function basis), while the at least one further image component is represented as an expansion in at least one further library. The libraries are complementary libraries if the representation of the quantitative absorption image in the at least one further library requires a significantly higher number of library functions than what is required when using the first library (and vice versa, i.e., the representation of the at least one further image component in the first library requires a significantly higher number of library functions than what is required when using the at least one further library). Advantageously, the expansion coefficients of the representation in the complementary libraries can be obtained with a minimization algorithm.

As a particular advantage, various types of image components can be separated from the absorption image as a result of the decomposing step. Preferably, the at the least one further image component comprises an excitation light fluence distribution image and/or a distribution of the optical scattering coefficient in the object. In this case, artifacts due to scattering of the energy deposition in the objects can be avoided. Alternatively, the at the least one further image component comprises an image representing a local polarization state (e.g., a birefringence or dichroism state of the object), an electric or magnetic field distribution, a speed of sound distribution, a dielectric constant distribution, a thermoelastic expansion coefficient distribution, and/or a heat capacity distribution in the object.

Particular benefits for medical imaging are achieved if the at least one further image component comprises an image representing a local state of the object, in particular a physiological state of biological tissue. The physiological state may represent, e.g., a disease progression, an oxygenation state and/or a metabolic state. As a further alternative, the at least one further image component may comprise an image representing a spatial distribution of a tissue bio-marker, e.g., an extrinsically administered molecular agent, a fluorescent protein, a functionalized particle, and/or a chromogenic assay in the object.

Further preferably, the provision of the thermoacoustic signals comprises a signal collection (measuring step). The object to be imaged is irradiated by electromagnetic energy, e.g., by laser pulses, and the thermoacoustic signals produced in response to the irradiation are recorded. Advantageously, the signal collection can be performed as it is known as such from conventional thermoacoustic imaging, in particular optoacoustic imaging. To this end, the signal collecting device comprises an electromagnetic energy source and an acoustic signal recording device with a detector array and/or a single detector, including at least one acoustic detection element. Preferably, an acoustically-matched membrane is provided separating the imaged object from a liquid medium such as, e.g., water or a physiological solution, where the at least one acoustic detection element is located. Advantageously, the membrane allows for the object to be imaged without being immersed into the liquid medium.

Advantageously, the imaging device can be provided with hardware circuits being configured to conduct the methods of above first or second aspects. As an example, the inversion circuit for matrix-based optoacoustic inversion of the thermoacoustic signals may include at least one of a matrix storage module storing the model matrix and/or its inverse or a truncated version of each (or both) of these matrices, containing the most energetic elements of these matrices, and an adjustment device being adapted for adjusting the model matrix in dependency on imaging conditions, e.g., on at least one of an acoustic heterogeneity of the object, a geometric profile of the illumination of the imaged object by the light pulses, a frequency and/or spatial response of a acoustic signal recording device utilized for collecting the thermoacoustic signals and an output of the decomposition device. Furthermore, the reconstruction device may comprise an iteration circuit being adapted for implementing an iterative propagation model-based simulation.

Further preferably, the acoustic signal recording device and the object are movable relative to each other. The steps of collecting the thermoacoustic signals, reconstructing the energy deposition image and decomposing the image can be repeated with varying geometric orientation and/or position of the signal recording device and the object relative to each other.

The decomposition step can be used as a first analysis step also in the Multi-Spectral Optoacoustic Tomography (MSOT) method. With regard to details of implementing the MSOT method, the subject matter of PCT/EP2008/006142 is incorporated herein by reference. Preferably, the decomposition is performed on, e.g., a difference between images obtained for different excitation wavelengths normalized by their sum. This eliminates possible negative effects of the spectral dependence of light fluence during spectral decomposition.

To effectively implement the proposed methods, appropriate geometries to optimally illuminate and collect data from tissues are required to ensure that sufficient amount of information is present. For example, the temporal and spatial resolutions with which the acoustic signals are measured preferably correspond to the desired pixel/voxel resolution in the reconstructed image. In addition, any parts of the object that are to be imaged preferably are illuminated as uniformly as possible for as many acoustic measurements as possible. This is preferred since the advantages of the method become apparent when achieving high quality whole-body (volumetric or cross-sectional) images but may not be essential for surface-limited imaging with relatively uniform excitation energy deposition, as is more commonly enabled currently. Therefore, system that can optimally implement the method is proposed as well, to illustrate the key components required for accurate implementation.

In contrast to the previous art, our method enables quantitative, rather than qualitative, mapping of the absorption coefficient, e.g., in biological tissue. As such, it is essential for in-vivo whole-body imaging applications, especially those dealing with deep tissue small animal imaging and clinical imaging. For the latter case, it is essential to provide also technology that effectively addresses aspects associated with volumetric imaging, i.e., imaging of large (compared to the light transport mean free path length (MFPL)) samples, when the actual optical properties of the imaged object and other experimental parameters are poorly determined or unknown or even varying during the course of the experiment.

We further provide a computer program residing on a computer-readable medium, with a program code for carrying out the methods described, and an apparatus comprising a computer-readable storage medium containing program instructions for carrying out the methods.

Further details and advantages are described in the following with reference to the attached drawings.

Preferred examples of our methods and devices are described in the following with reference to optoacoustic tomography. This disclosure is not restricted to the examples, but can be equally applied to other methods utilizing opto- or thermoacoustic interactions, for instance Photo-Acoustic Tomography (PAT), multispectral optoacoustic tomography (MSOT), thermoacoustic tomography (TAT) or Near-Field Radiofrequency Tomography (NRT).

1. Overview

Mapping the absorption coefficient of an object, e.g. a human or animal body or a part thereof using optoacoustic imaging can be described in three general steps. A schematic description of the steps is given in FIG. 1. The first step S1 comprises data acquisition and entails illuminating the imaged object using high-power short-pulse lasers and measuring the formed acoustic waves by detector located in proximity of the object's boundary, or stated otherwise, measuring the subsequent acoustic field around the object's boundary. Illuminating the object can optionally include multispectral illumination. The further two steps S2 and S3 are the core of our methods described herein and involve processing the measured data to obtain a two- or three-dimensional map of the optical absorption coefficient within the object. Conducting the second and third steps S2 and S3 immediately after the first signal collection step is an optional feature. Alternatively, the image reconstruction can be applied to data obtained from an image data storage and/or via a computer network.

In the second step S2, the model-based acoustic-inversion method is used to backtrack the acoustic wave propagation and find the optoacoustic sources that were created within the object as a result of pulsed light absorption, or stated otherwise, the second step S2 can involve recovering the acoustic sources within the imaged object from the measured acoustic fields on its boundary. Because the relation between the measured acoustic field and the optoacoustic sources is linear, it is preferred to discretize it into a matrix form to facilitate numerical calculations. The matrix may include all the linear effects involving the acoustic propagation and detection. For example, the frequency response of the acoustic detector, speed of sound heterogeneities, or acoustic attenuation and dispersion can be accounted for in the matrix relation. Once the matrix is calculated, various inversion schemes may be used for inverting the matrix relation and obtaining the distribution (image) of the optoacoustic sources within the object.

The optoacoustic sources' amplitudes are proportional to the amount of energy absorbed within the object. Thus, mapping the optoacoustic sources does not directly yields the absorption coefficient, but rather the product between the absorption coefficient and light fluence. As a result, the optoacoustic source image is biased toward the regions of the objects that are better lit. The third step S3 comprises eliminating this bias, thus obtaining an image of the absorption coefficient from the optoacoustic source image. This step S3 is based on the decomposition method that exploits the different spatial properties of the absorption coefficient and light fluence within the body which dictate different sparse representations for these two functions. Because of light diffusion, the fluence may be regarded as a slowly varying function, whereas the absorption coefficient may have sharp transients. Stated otherwise, step S3 can involve decomposing the acoustic-source into its two or more components: the light fluence and the absorption coefficient within the object and/or other components, e.g., distribution of a certain compound or biomarker. In multi-spectral measurements, the third step may be also applied to the normalized difference of optoacoustic images obtained for different excitation wavelengths. For example, for multispectral images, an additional step S4 can involve calculating a difference, a ratio, or any other combination between acoustic sources acquired at two or more illumination wavelengths.

Preferably, the method decomposes the optoacoustic image by calculating the sparsest representation of its logarithm over the unification of the two libraries. The sparsest representation can be found by using one of several available algorithms. In this representation, all the elements that are included in the library of the absorption coefficient can be used to effectively extract the quantified absorption coefficient image.

Figure 2:
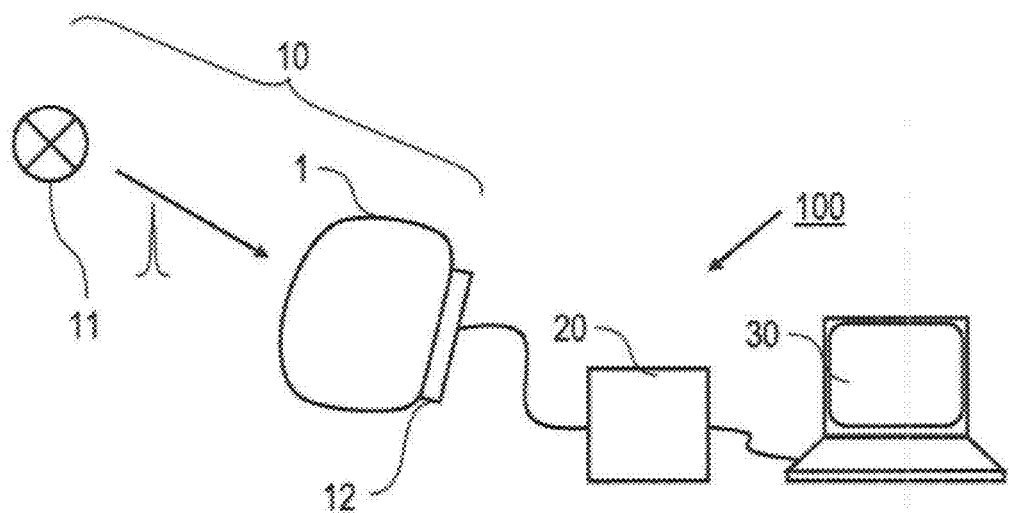
FIGS. 2 and 3 are schematic illustrations of examples of the imaging device.

FIG. 2 schematically illustrates an example of an imaging device 100 for thermoacoustic imaging of an object 1. The imaging device 100 comprises a signal collecting device 10, an image processor device 20 and optionally a further control device 30. The components 20, 30 can be implemented within a common hardware unit. The signal collecting device 10 comprises an electromagnetic energy source, like at least one laser source 11, emitting pulses with a duration lower than 50 ns and an acoustic signal recording device 12 (detector device) with at least one acoustic detection element. The laser source 11 can be tuned to different wavelengths so that multispectral information can be collected from the object 1, e.g., for localization of distinct spectral signatures of tissue biomarkers.

Details of the signal collecting device 10 can be implemented as described by D. Razansky and V. Ntziachristos in "Med. Phys.," Vol. 34, 2007, pp. 4293-4301. In particular, the laser source 11 may comprise a tunable optical parametric oscillator (OPO) laser providing <10 ns duration pulses with repetition frequencies in the range 10-100 Hz in the visible (400-700 nm) or near-infrared (700-1400 nm) spectra. As an example, the illumination wavelength was set to 750 nm while the output energy was kept below 25 mJ per pulse while the output near-infrared beam was expanded so its average diameter in the sample plane was about 2 cm.

To illuminate the region of interest in object 1 as uniformly as possible, the laser beam can be expanded to cover the entire object's diameter and split into two or more beams, illuminating the object 1 from different directions. Furthermore, delivery of light into the object 1 can be done by, e.g., optical fiber or fiber bundle having multiple arms or by means of transmitting free beams via optical arrangement of mirrors, beam splitters, diffusers and the like.

Figure 3:
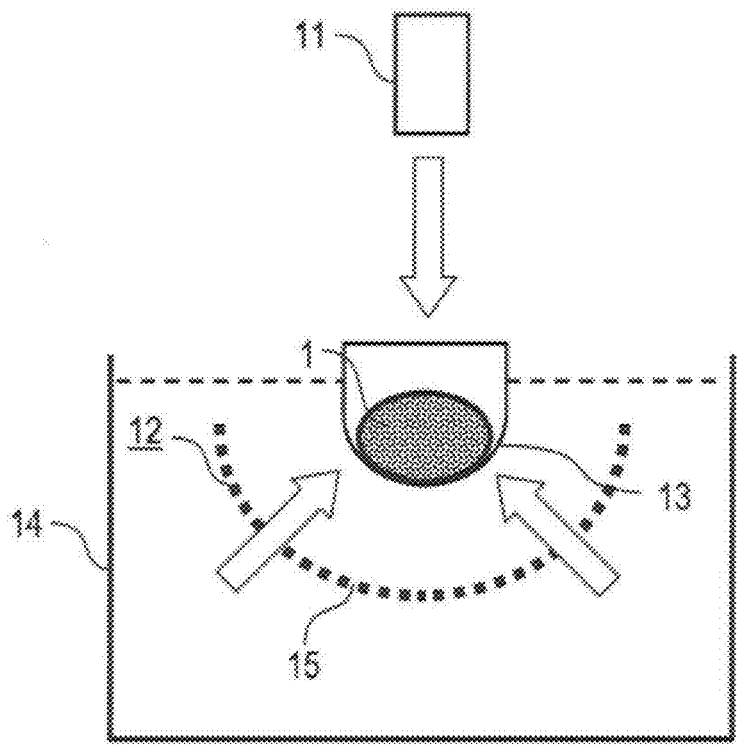

The acoustic signal recording device 12 is arranged in acoustic contact with a surface of the object, e.g., using a sound transmitting substance, like a gel, or a liquid. The object 1 can be partially or completely separated from the liquid as shown in FIG. 3. The acoustic signal recording device 12 comprises, e.g., a single piezoelectric-type point detector. For collection of the signals over 360° projections, the object 1 can be rotated on a stage with certain angular increments (e.g. 2 or 3 degrees), while the detector is placed at a distance of, e.g., 40 mm from the center of rotation. The acoustic signal recording device 12 can be translated along a vertical axis over a predetermined number of points to acquire data for three-dimensional reconstruction in cylindrical scanning configuration (see above publication of D. Razansky and V. Ntziachristos). The detector's surface can alternatively resemble different focusing shapes (e.g., cylindrical, spherical) so that the optoacoustic signals can be preferentially collected from different areas of interest (line, plane and the like). Due to ultrawideband nature of typical optoacoustic signals, the detector should ideally have a broad effective (−6 db) bandwidth, e.g., between 1-10 MHz, more preferably between 200 kHz-30 MHz, most preferably between 50 kHz-100 MHz. Alternatively, the acoustic signal recording device 12 comprises a detector array with a plurality of acoustic detection elements to simultaneously collect information from multiple projection angles. The detection of optoacoustic responses can alternatively be made by optical means, e.g., by using interferometric devices sensitive to pressure variations, e.g., Fabry-Perot films and other multi-layered structures.

As an example, the full-width-at-half-maximum (FWHM) of the detector's frequency response can be at 3.5 MHz, which corresponds to a diffraction-limited spatial resolution of about 200 μm. Frequency response of the detector does not only limit the spatial resolution of the reconstructed images, but can also distort the shape of the detected signals and thus introduce additional image artifacts. Therefore, the frequency response is taken into account during the reconstruction process (see below).

The time-resolved thermoacoustic signals (typically electrical voltage signals), recorded by the acoustic signal recording device 12 can be digitized, averaged (for noise suppression) and transmitted to the central processing unit (CPU) of the image processor device 20 responsible for quantitative image reconstruction.

According to FIG. 3, the object 1 illuminated with the laser source 11 is placed on top of a transparent membrane 13. The membrane 13 is made of optically transparent material that also does not significantly alter propagation of sound, e.g., acoustically-matched membrane made of polyvinyl chloride plastisol (PVCP) or thin films of polyethylene. In this way, an efficient transmission of both laser radiation and the induced optoacoustic response is facilitated. The membrane 13 also ensures that the imaged object 1 can be conveniently placed for imaging without direct contact with water. The membrane 13 is placed in contact with a water tank 14, into which the detector array 12 is immersed. The detector array 12 is a curved array with 64 acoustic detection elements 15, which form, for example, 180° arc that surrounds the object 1. In example of FIG. 3, all the acoustic detection elements 15 are cylindrically focused in the detection plane to allow for simultaneous collection of signals from a two-dimensional detection plane (drawing plane). The device will therefore collect two-dimensional data in real time.

Figure 4:
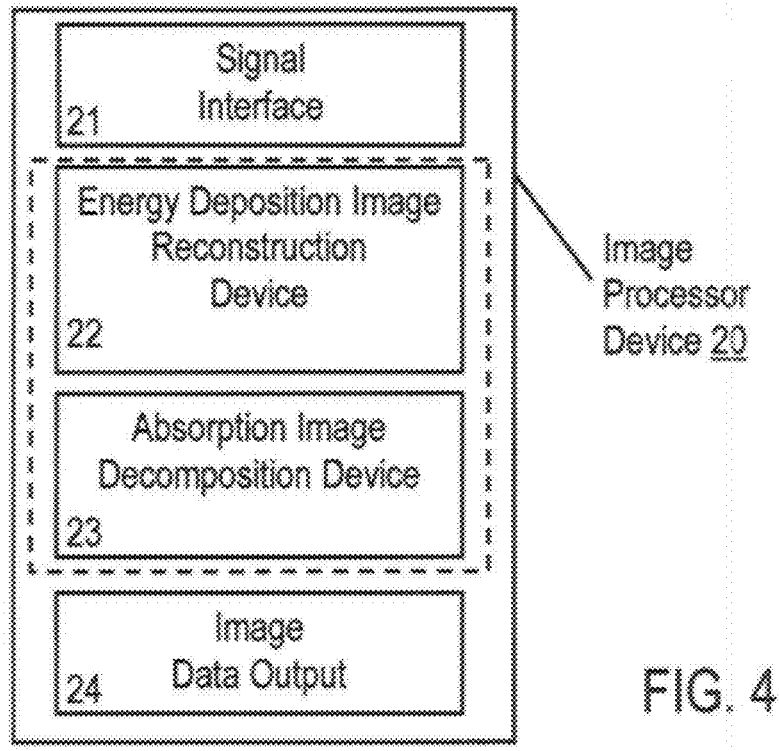
FIG. 4 is a schematic illustration of main components of a signal processor device included in the imaging device.

The main components of the image processor device 20 are illustrated in FIG. 4. After pre-processing collected raw signals in the signal interface unit 21, the thermoacoustic signals are delivered to the reconstruction device 22 quantitatively reconstructing the energy deposition image (see below 2.). Subsequently, the energy deposition image is processed in the decomposition device 23 decomposing the energy deposition image into a quantitative absorption image and at least one further image component (see below 3., 4.). Finally, the quantitative absorption image data are output via the interface 24, followed, e.g., by further data handling, like, e.g., a data storage, image data recording, image display or image output, like printing.

2. Semi-Analytical Model-Based Optoacoustic Inversion Method for Quantitative Thermoacoustic Tomography The forward problem of optoacoustic tomography amounts to modeling the acoustic fields created by the instantaneous heating and relaxation effect of the laser irradiation. Under the condition of thermal confinement, the temperature increase in each part of the irradiated object is not affected by temperature increase in neighboring regions, i.e., heat conductance is negligible. This condition is usually fulfilled for laser pulses with duration lower than 1 μs and guarantees that the acoustic sources created in the object are proportional to the absorbed optical energy. Under this condition, and neglecting acoustic losses, the propagation equation for the acoustic fields is given by $$\frac{\partial^2 p(r,t)}{\partial t^2} - c^2 \rho \nabla \cdot \left(\frac{1}{\rho} \nabla p(r,t)\right) = \Gamma \frac{\partial H(r,t)}{\partial t}, \quad (1)$$

where c and ρ are velocity of sound in tissue and its density, Γ is the Grüneisen parameter, and h is the amount of energy absorbed in the tissue per unit volume and per unit time. H can be represented as a product between its spatial and temporal components h, $h_t$. In the present analysis, propagation of acoustic fields in acoustically homogenous medium can be assumed. Under this assumption, the above equation takes the form of $$\frac{\partial^2 p(r,t)}{\partial t^2} - c^2 \nabla^2 p(r,t) = \Gamma h(r) \frac{\partial h_t(t)}{\partial t}. \quad (2)$$

In most practical cases, the duration of the optical pulse is short enough to be approximated by a delta function, namely $h_t(t) = \delta(t)$. In this case, i.e., assuming the heating due to the laser pulse is instantaneous, and that the medium is acoustically homogeneous, an analytical solution is given by a Poisson-type integral, wherein the acoustic pressure measured at a coordinate x and at a time t fulfills the following equation:

$$p(x,t) \propto \frac{\partial}{\partial t} \int_{R=vt} \frac{h(x')}{R} dA', \quad (3)$$

where R=|x−x'|, v is the velocity of sound in the medium, and h(x) is the optoacoustic image. When the measurement is performed in 3D, the integration in Eq. (3) is performed over a sphere. When the measurement is performed in 2D, the integration in Eq. (3) is performed over a circle. In the following description, the 2D case is illustrated, although the same concepts can be generalized for the 3D case. In particular, the solutions can be readily generalized to 3D by collecting optoacoustic signals that originate at different planes.

In a two-dimensional (2D) geometry, for which all the sources lie in a plane, the integration is performed over a circle. For a given sensor position r=($x_0$,$y_0$), the integral in Eq. (3) can be explicitly rewritten as $$\int_{R=ct} \frac{h(r')}{R} dA' = \int_{\theta_1}^{\theta_2} h(x_0 + R\cos\theta, y_0 + R\sin\theta) d\theta. \quad (4)$$

In both 2D and 3D geometries, the calculation of Eq. (4) poses numerical difficulties that stem from the inconsistency of the grid with the surface on which the integral is to be calculated. Calculating the derivative of the integral only exacerbates the numerical problems. Typically, to accurately calculate Eq. (4), the resolution of the grid should be considerably higher than what otherwise be required to accurately represent h(r). This readily results in computational inefficiency of the solution to the forward problem.

A grid is defined to discretely represent h(x), and the grid coordinates are marked by $x_i$. To calculate the integral in Eq. (3), a close form approximation h(x) is used for coordinates which are not on the grid. The only requirement for that approximation is that for any given coordinate x', the value of h(x') be a linear superposition of the values of h(x) at the mesh coordinates:

$$h(x') = \sum_{i=n}^{m} f_i(x_n, \ldots, x_m, x') h(x_i). \quad (5)$$

Since the mesh points are predetermined, the value of the function $f_i(x_n, \ldots, x_m)$ is independent of the measured data. Substituting Eq. (5) into Eq. (3), a linear connection between the measured acoustic pressure and the optoacoustic image is obtained:

$$p(x,t) \propto \sum_{i=k}^{l} g_i(x, t, x_k, \ldots, x_l) h(x_i), \quad (6)$$

where the values of $g_i(x,t,x_k, \ldots, x_l)$ are calculated by solving the integral in Eq. (3) with the functions $f_i(x_n, \ldots, x_m, x')$ as integrands.

Appropriate interpolation functions can be found as follows. The functions should be such that yield an analytical solution to the integral in Eq. (3). In addition, because of the derivative operator in Eq. (3), the interpolation functions should also be differentiable or piecewise differentiable. Preferably, a linear interpolation is used for which the resulting function $h_r(r)$ is piecewise planar.

Figure 5:
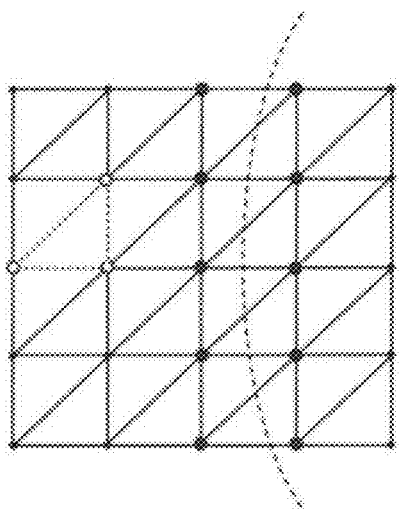
FIG. 5 is a graphical illustration of a grid used for tiling an x-y reconstruction plane.

The interpolation is performed by tiling the x-y reconstruction plane with right-angle triangles with vertexes on the grid point as exemplary illustrated in FIG. 5. For each coordinate ($x_i$,$y_i$) $h_r(i)$ is assigned as its elevation value on the z axis, i.e. $z_i$=$h_r(r_i)$. Accordingly, each triangle can be described by a set of the three coordinates of its vertices ($x_l$,$y_l$,$z_l$), ($x_n$,$y_n$,$z_n$) and ($x_m$,$y_m$,$z_m$). The interpolated values of $h_r(r)$ within each triangle are thus taken as the value of the plane elevation calculated via $$h_r(x, y) = -\frac{Ax + By + D}{C}, \tag{7}$$

where $$A = \begin{vmatrix} 1 & y_l & z_l \\ 1 & y_n & z_n \\ 1 & y_m & z_m \end{vmatrix}, B = \begin{vmatrix} x_l & 1 & z_l \\ x_n & 1 & z_n \\ x_m & 1 & z_m \end{vmatrix}, \tag{8}$$

$$C = \begin{vmatrix} x_l & y_l & 1 \\ x_n & y_n & 1 \\ x_m & y_m & 1 \end{vmatrix}, D = \begin{vmatrix} x_l & y_l & z_l \\ x_n & y_n & z_n \\ x_m & y_m & z_m \end{vmatrix}$$

and the operation |·| refers to matrix determinant. Substituting Eq. (7) into Eq. (4), one obtains $$\int_{R=ct} \frac{h(r')}{R} dA' = -C^{-1} \int_{\theta_1}^{\theta_2} [A(x_0 + R\cos\theta) + B(y_0 + R\sin\theta) + D] d\theta. \tag{9}$$

The integral in Eq. (5) can then be solved analytically within each triangle resulting in a linear function of $z_l$, $z_n$, and $z_m$. The coefficients of $z_l$, $z_n$, and $z_m$ are subsequently used to calculate $g_i(r,t)$.

Figure 6:
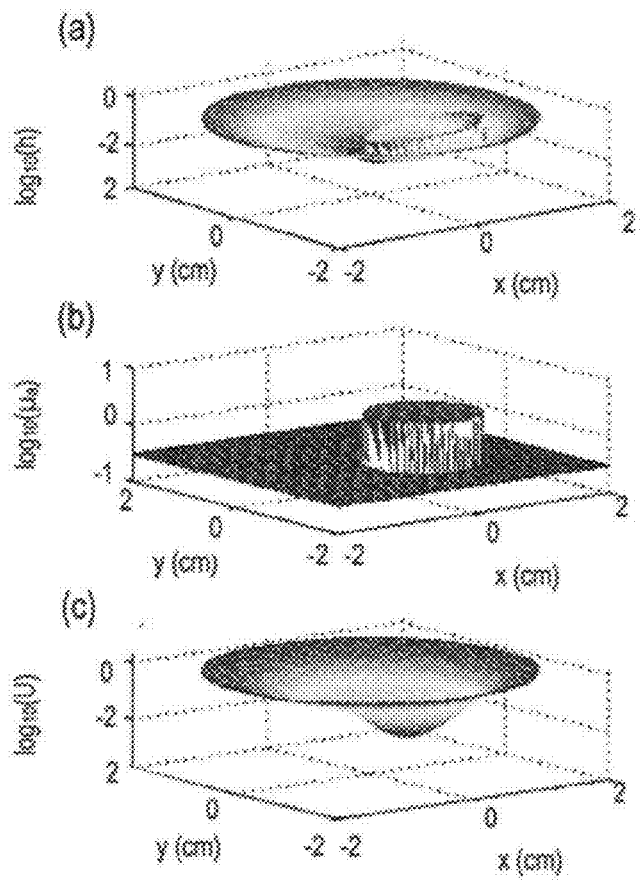
FIGS. 6 and 7 are graphical illustrations of different components in optoacoustic images and their sparse representation in complementary libraries.

With the example shown in FIG. 6, each grid point is assigned three coordinates. Each right-angle triangle represents a unit cell in which the image is interpolated linearly. An example of a unit cell is shown in dotted lines, where the value of the OAT is determined solely by the 3D coordinates of its vertex points: $(x_l, y_l, z_l)$, $(x_n, y_n, z_n)$, and $(x_m, y_m, z_m)$. The dashed curved line represents a certain arc on which the integral in Eq. (9) is calculated, and the large black grid points are the grid points that are involved in calculating the integral and correspond to the nonzero elements in Eq. (6).

Next, the spatial and temporal coordinates $\{(x_1, t_j)\}_j$ are defined over which the acoustic signal is acquired. Denoting $p_j = p(x_j, t_j)$ and $h_i = h(x_i)$, the following matrix equation is obtained:

$$p = Mh \tag{10}$$

where p is a vector whose elements are $p_j$, and $h$ is a vector whose element are $h_i$.

The elements in the matrix M are defined by the image grid, the measurement's spatial and temporal coordinates, and on the type of approximation being used. In particular, the elements in the matrix M are the corresponding values of $g_i(r,t)$. Thus, for a given optoacoustic imaging system, the matrix M does not depend on the imaged object, and thus can be pre-calculated before the experiment is performed.

When the frequency response of the acoustic detector is approximately known, it can be incorporated into the forward model. The frequency response is discretized and saved in a vector s. Then a diagonal matrix $M_s$ is constructed whose diagonal elements correspond to the elements in the vector s. F is denoted to be the one-dimensional discrete Fourier transform matrix, i.e. Fp is the discrete Fourier transform of p. Thus, the spectrum of the measured signals $p_s$ is given by $p_s = M_s Fp$ and fulfills the equation:

$$p_s = M_s FMh. \tag{11}$$

The optoacoustic inversion method may also include additional effects that appear in the system. If the imaged object is acoustically heterogeneous, and the sound velocity variations within the objects are known, they may be incorporated into the matrix equation. This can be achieved by recalculating the matrix M for the following equation instead of Eq. 3:

$$p(x, t) \propto \frac{\partial}{\partial t} \int_{S(t)} \frac{h(x')}{R} dA' \tag{12}$$

where S(t) is a curve or surface on which every point has the same time of flight t to the detector.

Another effect that can be incorporated in the matrix relation may result from variations in the illumination profile for different detector locations. Such variations can appear if the object is rotated with respect to the light source and the detectors. In that case, the integral in Eq. (12) should be generalized to $$p(x, t, \theta) \propto \frac{\partial}{\partial t} \int_{S(t,\theta)} \frac{U(x', \theta) h(x')}{R} dA', \tag{13}$$

where $U(x',\theta)$ is an estimation to the fluence within the object for the projection at angle $\theta$.

To recover the optoacoustic image h, Eq. (11) is inverted. Several methods exist to perform the inversion. The most common approach is based on using least square error techniques. In this approach, the vector h' which minimizes the following square error is found:

$$|p_s - M_s FMh'|_2^2. \tag{14}$$

Minimization can be performed using standard numerical techniques such as gradient descent, conjugate gradient, LSQR and the like. Alternatively, minimization may be performed by calculating the pseudo-inverse of the matrix $M_s FMh$. The advantage of using the pseudo-inverse is that is only depends on the system characteristics and not on the measured object. In this case, the reconstruction amounts to multiplying $p_s$ by a predetermined matrix. The model matrix is sparse, i.e., most of its elements are zero. This property may be used for improving the inversion process, as well as the matrix' storage.

When the measured data is insufficient for obtaining an accurate reconstruction, e.g., in the case in which some projections are unattainable, adaptive methods could be used to invert Eq. (11). As a first step, one needs to find a library in which the optoacoustic image is expected to be sparse. Once such a library is found, the optoacoustic image over the grid can be represented as $h = Q\alpha$, where $\alpha$ is a vector containing the coefficients of the for the library elements, and Q is the matrix defining the library elements. For a sparse representation of h, most of the elements in $\alpha$ should be close to zero. The inversion is performed by finding the sparsest signal that returns a low error for Eq. (12):

$$\min_\alpha \|\alpha\|_0 \text{ subject to } \|p_s - M_s FMQ\alpha\| < \in, \tag{15}$$

where $\in$ is the acceptable reconstruction error. Methods for solving the optimization problem of Eq. (15) are described in the following section 3.

Another way to address the reconstruction problem when only partial information is available is to add a regularization term to Eq. (14), or perform singular value decomposition. The last singular values in the decomposition, which may correspond to artifacts in the reconstructed image, may be truncated or attenuated by some function of the values or their corresponding eigen-images.

Numerical simulations (implemented in Matlab, Mathworks Inc., Natick, Mass., and executed on a Intel® Core™2 Quad Processors CPU operating at 2.67 GHz) have been performed for testing the matrix inversion method. As an example, an image with a size of some cm was reconstructed assuming a detector with a flat frequency response. The number of projections used for the inversion was 80 and the number of grid points was 80 for each axis. The temporal resolution which was used for the acoustic field was twice the corresponding spatial resolution. The run time for constructing and inverting the matrix was approximately 9 minutes. Once the inverse matrix was calculated, the reconstructed image was obtained in approximately 0.2 seconds. The matrix size was 20240×6400 and occupied approximately 1 GB of memory. Reconstructing an OAT image, for which an exact analytical representation of the generated acoustic signals exists attained an exact reconstruction of the image. The results have been compared with those using the conventional filtered back-projection algorithm, whereby strong artifacts appeared in the back-projection, which did not occur in the model-based reconstruction. In experimental tests, the run time for constructing and inverting the model matrix was approximately one hour for the given experimental setup. After calculating the inverse, recovery of an image for each experiment took only about 1.3 seconds. The inverse matrix's dimensions were 8281×24120 and it occupied approximately 3 GB of memory.

The optoacoustic image h reconstructed according to the above method can be further handled as the energy deposition image to be obtained. Preferably, the energy deposition image is subjected to the following decomposition.

3. Sparse-Representation Decomposition Method

To decompose the optoacoustic image into at least two of its components, a sparse representation method is used. The underlying concept of sparse representation is that natural signals can be sparsely represented in appropriate function bases or libraries, i.e., they can be represented as a sum of a small number of elementary functions. Sparse representation techniques have been proven useful for denoising, compression and compressed sensing (see, e.g., S. S. Chen et al. in "SIAM Review," Vol. 43, 2001, pp. 129-159).

The decomposition method is described in the following with exemplary reference to an image depending on the absorption coefficient and the further image component local light fluence in the object. Decomposing for separating other or further image components, like, e.g., a distribution of the optical scattering coefficient or a distribution of a certain biomarker can be conducted in an analogue way.

The optoacoustic image h(x, y) is proportional to the product of the absorption coefficient $\mu_a$(x, y) and local light fluence U(x, y): h(x, y)$\propto\mu_a$(x, y)U(x, y). To use sparse-representation techniques, the signal should first be transformed from a product formula to a sum formula. This is achieved by taking the logarithm of the optoacoustic image:

$$\log[h(x,y)] = \log[\mu_a(x,y)] + \log[U(x,y)] + \text{Const.} \quad (16)$$

The functions $\log[\mu_a(x, y)]$ and $\log[U(x, y)]$ have very distinctive characteristics that enable extracting both of them from $\log[h(x, y)]$. The function $\log[U(x, y)]$ is global and slowly varying, whereas the function $\log[\mu_a(x, y)]$ is local and may have fast variations. The global variation of the function $\log[U(x, y)]$ is smaller compared with the local variations of the function $\log[\mu_a(x, y)]$.

FIG. 6 illustrates in an exemplary manner a 3D mesh of (a) the optoacoustic image, (b) absorption coefficient, and (c) fluence for a model object (for printing reasons shown with grey values). FIG. 6 shows that the spatial properties of both the absorption coefficient, and fluence are distinguishable in the photoacoustic image. In particular, the features of both log $[\mu_a$(x; y)] and log [U(x; y)] are distinguishable in the function log [h(x; y)].

The decomposition of log [U(x, y)] is based on the assumption that two libraries $\{\phi_n\}_n$ and $\{\psi_n\}_n$ can be found which fulfill the following complimentary conditions:

1) The function log [$\mu_a$(x, y)] can be sparsely represented in $\{\phi_n\}$, but not in $\{\psi_n\}_n$.

2) The function log [U(x, y)] can be sparsely represented in $\{\psi_n\}_n$ but not in $\{\phi_n\}_n$.

These conditions will be called the sparsity conditions (or compatibility conditions) in the following. When the sparsity conditions are met, the optoacoustic image can be sparsely represented in the joint library $\{\phi_n, \psi_m\}_{n,m}$:

$$\log[h(x, y)] = \sum_{n=1}^{N} c_n \phi_n(x, y) + \sum_{m=1}^{M} d_m \psi_m(x, y). \quad (17)$$

Given the coefficients $c_n$ and $d_m$, log [$\mu_a$(x, y)] and log [U(x, y)] can be calculated using the following equations:

$$\log[\mu_a(x, y)] = \sum_{n=1}^{N} c_n \phi_n(x, y)$$

$$\log[U(x, y)] = \sum_{m=1}^{M} d_m \psi_m(x, y). \quad (18)$$

To decompose the optoacoustic image, two libraries (e.g., function bases) that fulfill the sparsity conditions are chosen.

For log [U(x, y)] the 2-dimensional discrete Fourier basis is preferred. The Fourier basis is very useful for sparse representation of smooth and global functions, such as log [U(x, y)], but cannot be used to sparsely represent functions with local details, such as log [$\mu_a$(x, y)].

The problem of finding a library that can sparsely represent general images, such as log [$\mu_a$(x, y)], has been extensively studied by the signal-processing community for the past decade. One possibility is to use the 2-dimensional discrete Haar wavelet basis to represent log [$\mu_a$(x, y)]. Haar wavelets are local, piecewise-constant functions and constitute the simplest library that can be used to sparsely represent natural images. We found that these wavelets are successful in sparsely representing images with discontinuities and are thus appropriate for representing log [$\mu_a$(x, y)] in particular when the optoacoustic image is of a phantom. Haar wavelets can also be used for optoacoustic images obtained in in vivo imaging of biological tissue. However, for such images, more complex dictionaries are preferred. The optimum library, in particular for sparsely representing natural images, can be selected in dependency on the imaging conditions and/or on the type of image being analyzed. The library may contain various distinct functions and function bases: translational variant or invariant wavelets (e.g., Haar wavelets, Daubechies wavelets, Coiflets and the like), curvelets, contourlets, edgelets, functions obtained through a learning process, user-defined functions and the like.

A priori information on the nature of the problem can further improve the choice of library. For example, when the image is expected to contain blood vessels, curvelets may be added to the library of the absorption coefficient, as they can sparsely represent one-dimensional curves. In addition functions can be defined manually or automatically according to the properties of the image. When the objects with well defined boundary appear in the image, one can detect the boundaries (manually or automatically) and assign a function that accepts a constant within the boundaries and zero outside them. These functions can also be added to the library of the absorption coefficient. One can also add elements to the library representing the light fluence. The inverse of the zero-th order modified Bessel function, which describes 2D propagation of light in scattering media, can be added: $1/I_0(\kappa |\vec{r} - \vec{a}|)$. Several values of K or a may be chosen corresponding to different attenuation rates and minimum fluence positions, respectively.

Because the decomposition is based on distinguishing between local and global properties, the background value of the absorption coefficient cannot be extracted. Thus, the reconstruction of log $[\mu_a(x, y)]$ is accurate up to an additive constant and the reconstruction of $\mu_a(x, y)$ is correct up to scaling. To scale an absorption coefficient that is obtained in an experiment, the experimental setup is calibrated. One way of doing so is by estimating the illumination on the surface of the object. This can be used to find $\mu_a(x, y)$ on the surface and recover the scaling factor. Another way would be to use a phantom with a known absorption to calibrate the system.

Figure 7:
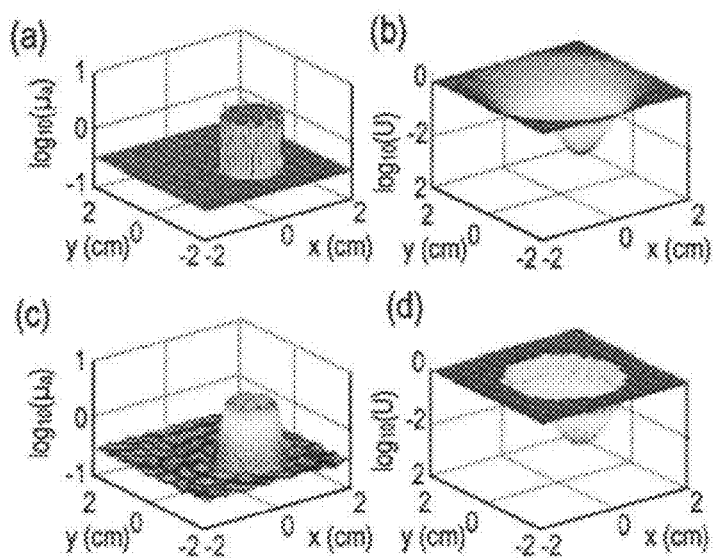

FIG. 7 illustrates in an exemplary manner that the combination of the Fourier and Haar bases fulfill the sparsity conditions. In the example, the functions were scaled to match the functions in FIG. 6. FIGS. 7a and 7b show the functions log $[\mu_a(x; y)]$ and log $[U(x; y)]$ (discretized and represented on a grid) calculated with only 200 and 100 elements respectively. The figure clearly shows that both functions can be sparsely represented in their respective bases. In FIGS. 7c and 7d the two functions are represented with the opposite bases and increased the number of elements to 250. The figure clearly shows that in spite of the increased number of elements, the functions were not well represented in the opposite bases.

Once two libraries that fulfill the sparsity condition are chosen, the decomposition problem is to find the minimum number of coefficients $c_n$ and $d_m$ that fulfill Eq. (17). In its discrete version the decomposition problem can be written in matrix form:

$$\min_\alpha |\alpha|_0 \text{ subject to } h = A\alpha \quad (19)$$

where $\alpha$ is a column vector whose elements are $c_n$ and $d_m$, $\alpha = [c_1, \ldots, c_n, d_1, \ldots, d_M]$; x is a column vector with $\log(h_k)$ as elements; and A is a K by (N+M) matrix whose columns correspond to the library functions $\phi_{n,k}$ and $\psi_{n,k}$. The zero norm $\|\cdot\|_0$ is the number of nonzero elements in a given vector. Because in practical cases, Eqs. (17) and (18) are mere approximations, Eq. (19) should be replaced by $$\min_\alpha |\alpha|_0 \text{ subject to } \|x - A\alpha\| < \in, \quad (20)$$

where $\in$ is the acceptable reconstruction error.

The optimization problem in Eq. (20) is non-convex, and generally can only be solved with non-polynomial complexity. Two notable methods to approximate the solution of Eq. (20) are the basis-pursuit and matching-pursuit algorithms. Basis pursuit is based on replacing the zero norm in Eq. (20) with the $l_1$ norm. In the $l_1$ norm, the problem is convex, and can be solved more efficiently than the zero-norm problem using linear programming. It has been shown that when the representation is sufficiently sparse, the results obtained by both norms are identical. Matching pursuit (MP) is an iterative algorithm for solving Eqs. (19) and (20). In MP, one iteratively builds the image from the elements of the original library. In each step, one element from the library is added to the representation of the image. The iterations stop once the signal is represented with sufficient accuracy or when the number of iterations has been exceeded. A variation of MP, called orthogonal matching pursuit (OMP) may also be used.

The main difference between the two MP algorithms is in the way in which the coefficients for the chosen library elements are calculated. In standard MP, the coefficient of each library element is chosen only once—when the element is added to the signal representation. Thus, errors in any of the iterative steps cannot be corrected in the further iterations. In OMP, the optimal coefficients for all the elements are recalculate for each iterations, thus allowing compensation for errors in early iterations.

After Eq. (20) has been solved, a solution vector $\alpha_I$ (I indicating the size of the vector) is obtained in which most elements are equal to zero (or are very close to zero), and a reduced matrix $A_I$ is obtained which contains only those rows of A which correspond to the nonzero elements in $\alpha_I$.

From the matrix $A_I$, two new matrices B and C are constructed. The matrices B and C are composed out of the columns of $A_I$ corresponding to the absorption coefficient basis $\{\phi_n\}_n$ and fluence basis $\{\psi_n\}_n$, respectively. Accordingly, two vectors $\beta$ and $\gamma$ are constructed out of $\alpha_I$. The vector representation of log $[\mu_a(x, y)]$ and, log $[U(x, y)]$ denoted by b and c respectively, is calculated using the following equations:

$$b = B\beta$$

$$c = C\gamma \quad (21).$$

The local absorption coefficient image $\mu$ reconstructed according to the above method can be further processed with conventional image processing or data handling techniques.

Numerical simulations conducted with examples like in FIG. 7 and with a more complex-shaped absorption coefficient image have proved that the reconstruction is capable to recover the absorption coefficient image of the object even if the model data are superimposed with noise data. Furthermore, the method was successfully tested in experiment with a tissue-mimicking phantom, resembling typical small-animal whole-body imaging configuration and the corresponding tissue properties and other experimental parameters.

4. Normalization And Application to MSOT

When optoacoustic images are taken for different excitation wavelengths, the decomposition may be applied not only to the images themselves, but also to normalized differences and/or ratios between different images and their combinations. For example, if two optoacoustic images $h_1$ and $h_2$ were acquired at two different illumination wavelength, one can denote their difference by dh and their sum by h. Assuming dh<<h, the following relation is obtained:

$$dh = (d\mu)U + (dU)\mu \quad (22).$$

Equation (22) shows that the differential optoacoustic image depends both on the average fluence as well as on the change in fluence. Normalizing the differential image by the average image results in:

$$\frac{dh}{h} = \frac{d\mu}{\mu} + \frac{dU}{U}. \quad (23)$$

The normalized differential image is a sum of two distinct images: one of the absorption coefficients and one of the light fluences. As a result, the same argument that allowed the decomposition of single optoacoustic images applies also here. By using the decomposition algorithm on dh/h, both $d\mu/\mu$ and $dU/U$ can be extracted. Since $\mu$ and U can be obtained from decomposing the original optoacoustic images, they can be used to finally obtain dμ and dU. Eq. (23) can be written in an alternative logarithmic form:

$$d \log h = d \log \mu + d \log U. \quad (24)$$

The same analysis can be used for both forms.

The ability to accurately extract changes in the absorption coefficient allows for spectral fitting to be performed, which can be used to calculate the concentration of various substances with spectrally varying absorption coefficient. Given a set of optoacoustic images $h_1, h_2, \ldots, h_n$, obtained for consecutive wavelengths $\lambda_1, \lambda_2, \ldots, \lambda_n$, the differential absorption coefficients $d\mu_1 = \mu_1 - \mu_2, \ldots, d\mu_{n-1} = \mu_{n-1} - \mu_n$ can be calculated using the process described above. The set $\{d\mu_1, d\mu_2, \ldots, d\mu_{n-1}\}$ together with the absorption coefficient at any other of the measurement's wavelengths, uniquely determines the set of absorption coefficients for all the measured wavelengths $\{\mu_1, \mu_2, \ldots, \mu_n\}$. Each of the two sets, or any of their processed versions, can be used as input for spectral fitting algorithms that determine the concentration of different substances according to their absorption spectrum. The spectral fitting can be obtained by minimizing the following square error:

$$\sum_{n'=1}^{n} \left| \sum_{k'=1}^{k} \eta_{k'} S_{k'}(\lambda_{n'}) - \mu_{n'} \right|^2 \quad (25)$$

where $\eta_{k'}$ is the concentration of substance k' and $S_{k'}(\lambda_{n'})$ is its absorption spectrum for the wavelength $\lambda_{n'}$. The spectral fitting can be performed by other methods known in the prior art, such as principle components analysis, independent component analysis or other types of source separation. The sparsity of the images may also be used in the fitting.

5. Preferred System Features

Figure 8:
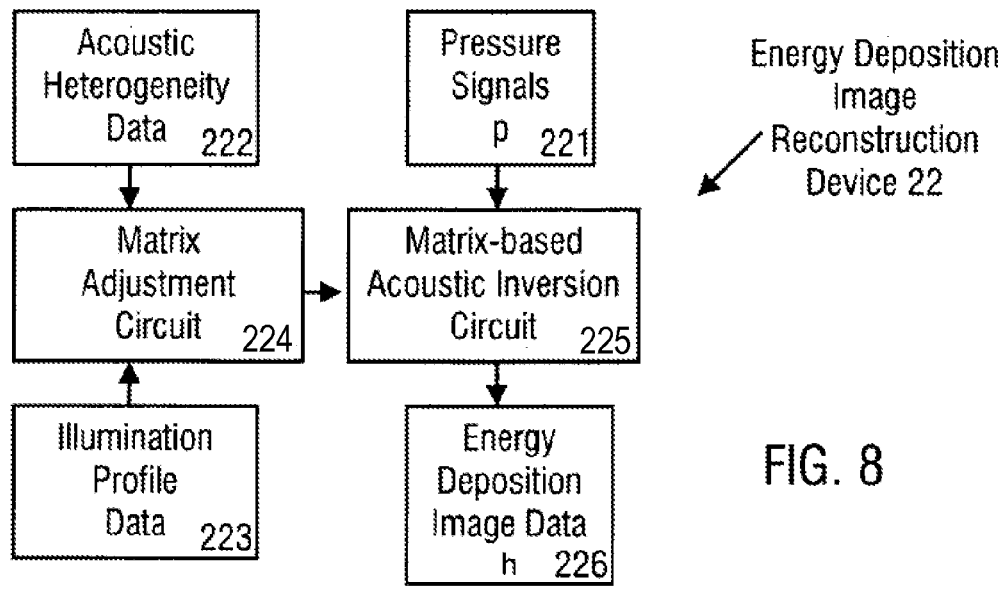
FIGS. 8 and 9 are schematic illustrations of alternative variants of an energy deposition reconstruction device included in the imaging device.

FIG. 8 schematically illustrates further configuration details of the image reconstruction device 22 conducting the optoacoustic inversion method (see section 2.). The image reconstruction device 22 comprises a first input device 221 receiving pressure signals from the signal collecting device 10 (see FIG. 1), at least one second input device 222, 223 receiving measurement conditions for adjusting the propagation matrix, a matrix adjustment circuit 224, an optoacoustic inversion circuit 225, and an image data output 226. The optoacoustic inversion circuit 225 is configured for implementing the above inversion of equation (11), e.g., based on the minimization of equation (14). Integration of the matrix adjustment circuit 225 into the image reconstruction device 22 is not strictly necessary. The propagation matrix can be pre-calculated separately and input to the optoacoustic inversion circuit 224 without additional adjustment.

Figure 9:
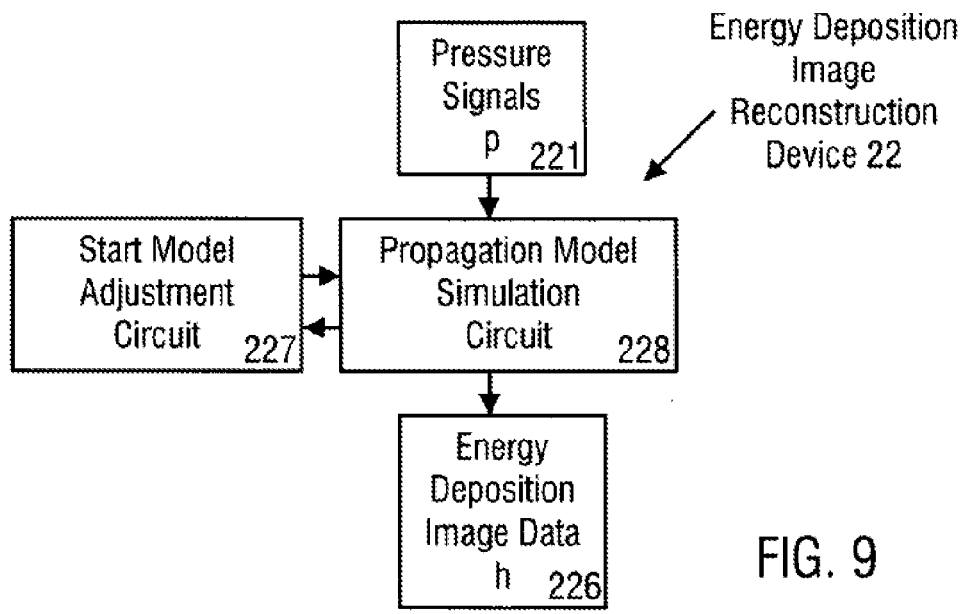

As mentioned above, the reconstruction of the energy deposition image may comprise a conventional analytical or numerical method, e.g., an iterative propagation model based simulation. FIG. 9 schematically illustrates a correspondingly adapted example of the image reconstruction device 22, which comprises an input device 221 receiving pressure signals from the signal collecting device 10 (see FIG. 1), a start model adjustment circuit 227, a propagation model simulation circuit 228, and an image data output 226. The propagation model simulation circuit 228 is configured for implementing the iterative propagation model based simulation of the pressure signals.

Figure 10:
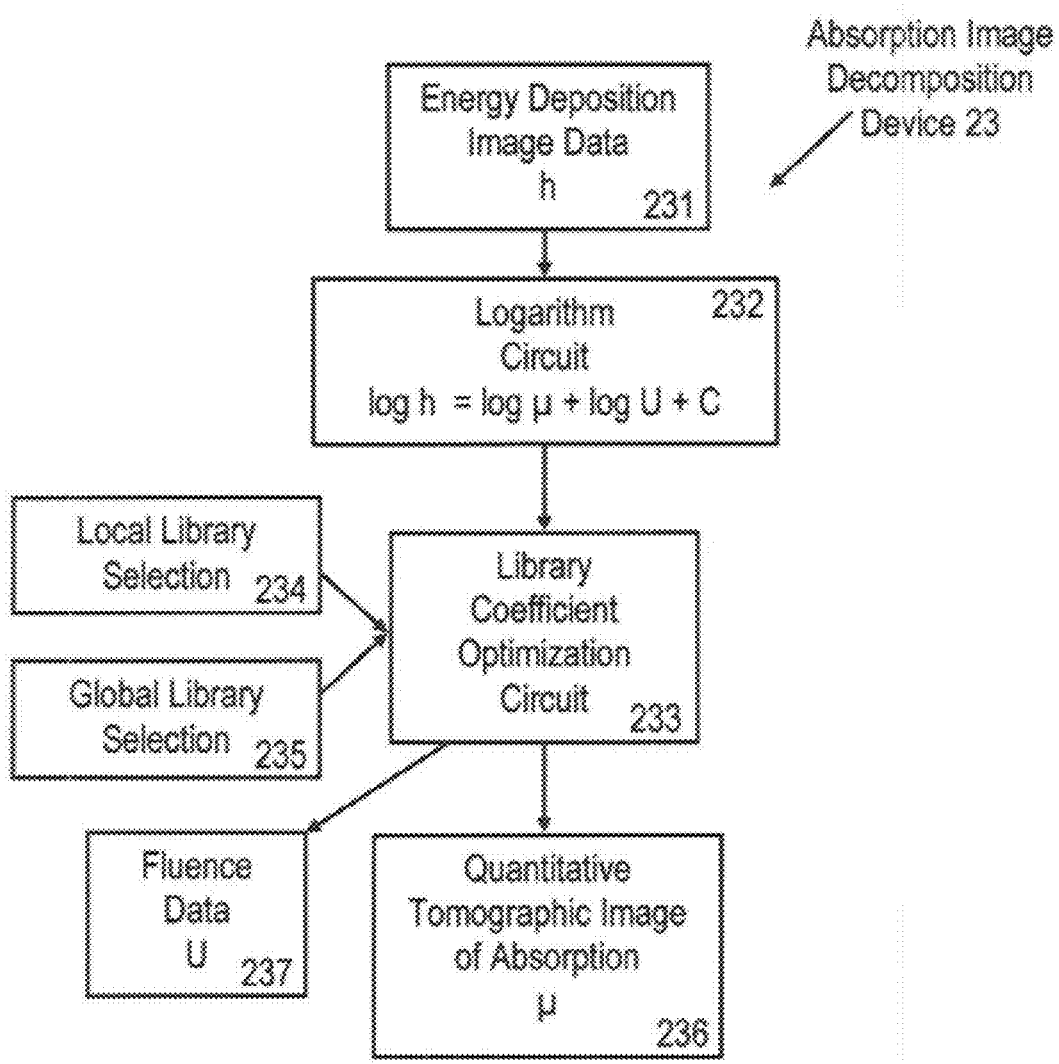
FIG. 10 is a schematic illustration of main components of an absorption image decomposition device included in the imaging device.

According to FIG. 10, the absorption image decomposition device 23 conducting the decomposition method (see section 3) comprises an energy deposition image data input 231, a logarithm circuit 232, a library coefficient optimization circuit 233 and first and second outputs 236, 237 delivering the decomposed image components comprising the absorption coefficient image and, e.g., the fluence image, resp. The library coefficient optimization circuit 233 is connected with a local library selection circuit 234 and a global library selection circuit 235.

The features in the above description, the drawings and the appended claims can be of significance both individually as well in combination for the realization of the methods and devices in its various forms.

The invention claimed is:

1. A method of thermoacoustic imaging of an object, the method comprising:
    pre-calculating, with a processor, a forward model matrix M that represents a relation between (i) absorption of electromagnetic energy within the object and (ii) pressure signals generated in response to said absorption of electromagnetic energy within the object, the forward model matrix M satisfying a forward model matrix equation expressed as p=Mh, wherein h is a vector having a plurality of elements $h_i$ that correspond to respective amounts $h(x_i)$ of electromagnetic energy absorbed at respective grid coordinates $x_i$ within the object and p is a vector having a plurality of elements $p_j$ corresponding to respective pressures $p(x_j, t_j)$ at respective coordinates $x_j$ at respective times $t_j$;
    irradiating, with an electromagnetic enemy source, the object with a quantity of electromagnetic energy;
    detecting, with at least one acoustic detection element, pressure signals generated in response to said absorption of the quantity of electromagnetic energy within the object;
    generating a data vector that contains the detected pressure signals;
    reconstructing an energy deposition image of the object by inverting the forward model matrix equation p=Mh to recover the vector h by either of:
        calculating, with said processor, a pseudo-inverse of the forward model matrix M and multiplying the pseudo-inverse of the forward model matrix M with the data vector; or
        using the data vector as the vector p in the forward model matrix equation p=Mh and performing, with said processor, a least square error minimization of the forward model matrix equation p=Mh; and
    outputting via an interface of said processor the energy deposition image to a control device that is configured to perform further data handling of the energy deposition image, said further data handling comprising displaying the energy deposition image.

2. The imaging method according to claim 1, wherein the forward model matrix M is adjusted in dependency on at least one of: an acoustic heterogeneity of the object, a geometric profile of illumination of the imaged object by light pulses, or a frequency response of the detector device via which said detecting pressure signals is accomplished.

3. The imaging method according to claim 1, wherein the forward model matrix M has elements corresponding to values that are calculated by solving an integral expressed as $$p(x, t) \propto \frac{\partial}{\partial t} \int_{R=vt} \frac{h(x')}{R} dA',$$

where $R=|x-x'|$, v is the velocity of sound in the object, $dA'$ is an element of a sphere or a circle, and $$h(x') = \sum_{i=n}^{m} f_i(x_n, \ldots, x_m, x')h(x_i)$$

is a close form approximation of $h(x_i)$, wherein for a given coordinate x' the value of h(x') is a linear superposition of the values of $h(x_i)$ at the grid coordinates $x_i$.

4. The imaging method according to claim 3, wherein solving the integral proceeds over a surface that is inconsistent with the grid coordinates $x_i$ such that certain coordinates x' are spaced apart from the grid coordinates $x_i$.

5. The imaging method according to claim 3, wherein the grid coordinates $x_i$ are predetermined, and wherein calculation of the function $f(x_n, \ldots, x_m)$ is independent of the detected pressure signals contained in the data vector.

6. The imaging method according to claim 5, wherein said pre-calculating the forward model matrix M takes place before said irradiating the object with the quantity of electromagnetic energy.

7. The imaging method according to claim 3, wherein $f_i(x_n, \ldots, x_m, x')$ are differentiable or piecewise differentiable interpolation functions.

8. An imaging device for thermoacoustic imaging of an object, the device comprising:
an electromagnetic energy source configured to irradiate the object with a quantity of electromagnetic energy;
at least one acoustic detection element configured to detect pressure signals representing a mechanical wave response to the irradiation of the object with the quantity of electromagnetic energy; and
an image processor configured to reconstruct an energy deposition image representing a local energy deposition within the object based on the detected pressure signals by:
pre-calculating a forward model matrix M that represents a relation between (i) absorption of electromagnetic energy within the object and (ii) pressure signals generated in response to said absorption of electromagnetic energy in the object, the forward model matrix M satisfying a forward model matrix equation expressed as p=Mh, wherein h is a vector having a plurality of elements $h_i$ that correspond to respective amounts $h(x_i)$ of electromagnetic energy absorbed at respective grid coordinates $x_i$ within the object and p is a vector having a plurality of elements $p_j$ corresponding to respective pressures $p(x_j, t_j)$ at respective coordinates $x_j$ at respective times $t_j$; and
inverting the forward model matrix equation p=Mh to recover the vector h using the detected pressure signals by either:
calculating a pseudo-inverse of the forward model matrix M and multiplying the pseudo-inverse of the forward model matrix M with a data vector that contains the detected pressure signals; or
using the data vector that contains the detected pressure signals as the vector p in the forward model matrix equation p=Mh and performing a least square error minimization of the forward model matrix equation p=Mh,
wherein the image processor comprises an interface via which the image processor is configured to output the energy deposition image to a control device that is configured to perform further data handling of the energy deposition image, said further data handling comprising displaying the energy deposition image.

9. The imaging device according to claim 8, wherein the mage processor comprises a digital storage medium configured to store the forward model matrix M.

10. The imaging device according to claim 8, wherein the electromagnetic energy source comprises an illumination device that illuminates the object by electromagnetic pulses.

11. The imaging device according to claim 8, wherein the at least one acoustic detection element corn rises at least one of a detector array and a single detector.

12. The imaging device according to claim 8, wherein the at least one acoustic detection element and the object are movable relative to each other.

13. The imaging device according to claim 8, wherein the image processor is configured to adjust the forward model matrix in dependency on at least one of: an acoustic heterogeneity of the object, a geometric profile of an illumination of the object via light pulses, or a frequency response of the at least one acoustic detection element.

14. The imaging device according to claim 8, wherein the forward model matrix M includes elements corresponding to values that are calculated by solving an integral expressed as $$p(x,t) \propto \frac{\partial}{\partial t} \int_{R=vt} \frac{h(x')}{R} dA',$$

where $R=|x-x'|$, v is the velocity of sound in the object, $dA'$ is an element of a sphere or a circle, and $$h(x') = \sum_{i=n}^{m} f_i(x_n, \ldots, x_m, x')h(x_i)$$

is a close form approximation of $h(x_i)$, wherein for a given coordinate x' the value of h(x') is a linear superposition of the values of $h(x_i)$ at the grid coordinates $x_i$.

15. The imaging device according to claim 14, wherein $f_i(x_n, \ldots, x_m, x')$ are differentiable or piecewise differentiable functions.

16. A method of thermoacoustic imaging of an object to be imaged, the method comprising:
pre-calculating, with a processor, a forward model matrix M that represents a relation between (i) absorption of electromagnetic energy within the object and (ii) pressure signals generated in response to said absorption of electromagnetic energy in the object, the forward model matrix M satisfying a forward model matrix equation expressed as p=Mh, wherein h is a vector having a plurality of elements each corresponding to an amount of electromagnetic energy absorbed at a discrete spatial grid coordinate and p is a vector having a plurality of elements each corresponding to a pressure value at both a spatial coordinate of a detector device and a temporal coordinate, wherein said pre-calculating the forward model matrix M does not depend on the object;
irradiating, with an electromagnetic energy source, the object with a quantity of electromagnetic energy;
detecting, with at least one acoustic detection element, pressure signals generated in response to an absorption of the quantity of electromagnetic energy in the object;
generating a data vector that contains the detected pressure signals;

reconstructing an energy deposition image by inverting the forward model matrix equation p=Mh to recover the vector h by calculating, with the processor, a pseudo-inverse of the forward model matrix M and multiplying the pseudo-inverse of the forward model matrix M with the data vector; and outputting via an interface of said processor the energy deposition image to a control device that is configured to perform further data handling of the energy deposition image, said further data handling comprising displaying the energy deposition image.

17. The method according to claim 16, wherein each discrete spatial grid coordinate is at a position within the object at which an amount of electromagnetic energy is absorbed when said irradiating the object with the quantity of electromagnetic energy takes place.

18. The method according to claim 16, wherein:
the vector h has elements $h_i$ corresponding to an amount $h(x_i)$ of electromagnetic energy absorbed at a grid coordinate $x_i$ in the object;
the vector p has elements $p_j$ corresponding to a pressure $p(x_j, t_j)$ at a coordinate $x_j$ at a time $t_j$; and
pre-calculating the forward model matrix M comprises solving an integral expressed as $$p(x, t) \propto \frac{\partial}{\partial t} \int_{R=vt} \frac{h(x')}{R} dA',$$

in which $R=|x-x'|$, v is the velocity of sound in the object, dA' is an element of a sphere or a circle, and $$h(x') = \sum_{i=n}^{m} f_i(x_n, \ldots, x_m, x') h(x_i)$$

is a close form approximation of $h(x_i)$, wherein for a given coordinate x' the value of h(x') is a linear superposition of the values of $h(x_i)$ at grid coordinates $x_i$, and wherein $f_i(x_n, \ldots, x_m, x')$ are differentiable or piecewise differentiable interpolation functions.

19. The method according to claim 16, wherein the relation between said absorption of electromagnetic energy within the object and said pressure signals generated in response to said absorption of electromagnetic energy in the object is expressed as $$p(x, t) \propto \sum_{i=k}^{l} g_i(x, t, x_k, \ldots, x_l) h(x_i),$$

wherein p(x, t) represents a pressure at a coordinate x at a respective time t, wherein $h(x_i)$ represents an amount of electromagnetic energy absorbed at a respective grid coordinate $x_i$ within the object, and wherein elements of the forward model matrix M are the values of $g_i(x, t, x_k, \ldots, x_l)$, which values are calculated by solving an integral with interpolation functions as integrands thereof.

20. The method of claim 19, wherein the values of $g_i(x, t, x_k, \ldots, x_l)$ are calculated by solving an integral expressed as $$p(x, t) \propto \frac{\partial}{\partial t} \int_{R=vt} \frac{h(x')}{R} dA'$$

with interpolation functions defined as $f_i(x_n, \ldots, x_m, x')$ as the integrands, wherein $R=|x-x'|$, v is the velocity of sound in the object, dA' is an element of a sphere or a circle, and $$h(x') = \sum_{i=n}^{m} f_i(x_n, \ldots, x_m, x') h(x_i)$$

is a close form approximation of $h(x_i)$, wherein for a given coordinate x' the value of h(x') is a linear superposition of the values of $h(x_i)$ at grid coordinates $x_i$.

21. The method of claim 20, wherein $f_i(x_n, \ldots, x_m, x')$ are differentiable or piecewise differentiable interpolation functions.

22. The method according to claim 16, wherein the forward model matrix M is calculated before the object is irradiated with the quantity of electromagnetic energy.

* * * * *